(12) United States Patent
Guo et al.

(10) Patent No.: US 8,754,099 B2
(45) Date of Patent: Jun. 17, 2014

(54) OXADIAZOLE BETA CARBOLINE DERIVATIVES AS ANTIDIABETIC COMPOUNDS

(75) Inventors: Liangqin Guo, Edison, NJ (US); William K. Hagmann, Westfield, NJ (US); Shuwen He, Edison, NJ (US); Zhong Lai, Scotch Plains, NJ (US); Jian Liu, Edison, NJ (US); Ravi P. Nargund, East Brunswick, NJ (US); Shrenik K. Shah, Metuchen, NJ (US); Quang T. Truong, Morganville, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 0 days.

(21) Appl. No.: 13/518,015

(22) PCT Filed: Jan. 11, 2011

(86) PCT No.: PCT/US2011/020796
§ 371 (c)(1),
(2), (4) Date: Jun. 21, 2012

(87) PCT Pub. No.: WO2011/088025
PCT Pub. Date: Jul. 21, 2011

(65) Prior Publication Data
US 2012/0264777 A1 Oct. 18, 2012

Related U.S. Application Data

(60) Provisional application No. 61/295,265, filed on Jan. 15, 2010.

(51) Int. Cl.
*A61K 31/44* (2006.01)
(52) U.S. Cl.
USPC .......................................................... 514/292
(58) Field of Classification Search
None
See application file for complete search history.

(56) References Cited

U.S. PATENT DOCUMENTS

| 6,586,445 B1 | 7/2003 | Thurieau et al. |
| 6,861,430 B2 | 3/2005 | Troxler et al. |

FOREIGN PATENT DOCUMENTS

| WO | 02/081471 A1 | 10/2002 | |
| WO | 03/010419 A1 | 2/2003 | |
| WO | 2009/011836 A | 1/2009 | |
| WO | WO 2009/011836 | * 1/2009 | ........... A61K 31/535 |

OTHER PUBLICATIONS

Williams et al (Foye's Principles of Medicinal Chemistry, 5th Edition, pp. 59-63, 2002).*
Anderson (Chem and Biol 10:787-797, 2003).*
Thiel (Nature Biotechnol 2:513-519, 2004).*
Banziger, M. et al., The development of a practical synthesis of the potent and selective somatostatin sst3 recptor antagonist [4-(3,4-difluoro-phenyl)-piperazine-1-yl]-[(4S,4aS,8aR)-2[(S)-3-(6-methoxy-pyridin-3-yl)-2-methyl-propyl]-decahydroisoquinoline-4-yl)-methanone (NVP-ACQ090), Tetrahedron, 2003, p. 3469-3477, vol. 14.
Bowlby, M. R. et al., "hERG (KCNH2 or Kv11.1) K Channels: Screening for Cardiac Arrhythmia Risk", Current Drug Metabolism, 2008, p. 965-997-, vol. 9.
Butler, A. E. et al., "B-Cell Deficit and Increased B-Cell Apoptosis in Humans With Type 2 Diabetes", Diabetes, 2003, p. 102-, vol. 52.
Crider, A. M., "Somatostatin receptor agonist and antagonists", Expert Opin. Ther. Patents, 2003, p. 1427-1441, vol. 13, No. 9.
Gordon, T. et al., "Peptide Azoles: A New Class of Biologically-Active Dipeptide Mimetics" Bioorganic & Medicinal Chemistry Letters. 1993, p. 915-920, vol. 3, No. 5.
Gordon, T. D. et al., "Synthetic Approaches to the 'Azole' Peptide Mimetics", Tetrahedron Letters, 1993, p. 1901-1904, vol. 34, No. 12.
Hocart, S. J. et al., "Potent Antagonists of Somatostatin: Synthesis and Biology", J. Med.Chem. 1998. p. 1146-1154, vol. 41.
Lagrutta, A. A. et al., "The hERG Channel and Risk of Drug-Acquired Cardiac Arrhythmia: An Overview" Current Topics in Medicinal Chemistry, 2008, p. 1102-1112. vol. 8.
Lahlou, H. et al., "Molecular Signaling of Somatostatin Receptors", Ann. Ny. Y. Acad. Sci. 2004, p. 121-131, vol. 1014.
Patel, Y. C., "Somatosttin and Its Receptor Family", Frontiers in Neuroendocrinology, 1999, p. 157-198, vol. 20.
Poitout, L. et al., "Identification of Potent Non-Peptide Somatostatin Antagonists with sst3 Selectivity", J. Med. Chem., 2001, p. 2990-3000, vol. 44.

(Continued)

*Primary Examiner* — Craig Ricci
(74) *Attorney, Agent, or Firm* — Baerbel R. Brown; Catherine D. Fitch

(57) ABSTRACT

Beta-carboline derivatives of structural formula I are selective antagonists of the somatostatin subtype receptor 3 (SSTR3) and are useful for the treatment of Type 2 diabetes mellitus and of conditions that are often associated with this disease, including hyperglycemia, insulin resistance, obesity, lipid disorders, and hypertension. The compounds are also useful for the treatment of depression and anxiety.

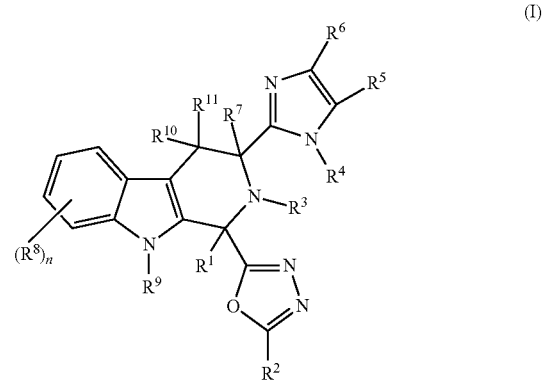

(I)

17 Claims, No Drawings

(56) References Cited

OTHER PUBLICATIONS

Polonsky, K.S., "Dynamics if insulin secretion on obesity and diabetes", International Journal of Obesity, 2000, p. S29-S31, vol. 24, Suppl 2.

Recanatini, M. et al., "QT Prolongation Through hERG K Channel Blockade: Current Knowledge and Strategies for the Early Prediction During Drug Development", Medicinal Research Reviews, 2005, p. 133-166, vol. 25, No. 2.

Reisine, T. et al., "Molecular Biology of Somatostation Receptors", Endocrine Reviews, 1995, p. 427-. vol. 16, No. 4.

Rfubi, J. C. et al., "SS3-selective potent peptides somatostation receptor antaginists", PNAS, 2000, p. 13873-13978, vol. 97, No. 25.

Dennis, A. et al., hERG channel trafficking: novel targets in drug-induced long QT syndrome, Biochemical Society Transactions, 2007, p. 1060-, vol. 35, Part 5.

NIH Publication No. 01-3670, Third Report of the National Cholesterol Education Program (NCEP) Expert Panel on Detection Evaluation, and Treatment of High Blood Cholesterol in Adults (Adult Treatment( Panel III), May 2001.

* cited by examiner

OXADIAZOLE BETA CARBOLINE DERIVATIVES AS ANTIDIABETIC COMPOUNDS

CROSS-REFERENCE TO RELATED APPLICATIONS

This application is a U.S. National Phase application under 35 U.S.C. §371 of PCT Application No. PCT/US2011/020796, filed 11 Jan. 2011, which claims priority from and the benefit of U.S. Provisional Application No. 61/295,265, filed Jan. 15, 2010.

FIELD OF THE INVENTION

The instant invention is concerned with substituted beta-carboline derivatives, which are selective antagonists of the somatostatin subtype receptor 3 (SSTR3) which are useful for the treatment of Type 2 diabetes mellitus and of conditions that are often associated with this disease, including hyperglycemia, insulin resistance, obesity, lipid disorders, and hypertension. The compounds are also useful for the treatment of depression and anxiety.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced by islet cells in the pancreas. Patients having Type 2 diabetes have resistance to the effects of insulin in stimulating glucose and lipid metabolism in the main insulin-sensitive tissues, including muscle, liver and adipose tissues. These patients often have normal levels of insulin, and may have hyperinsulinemia (elevated plasma insulin levels), as they compensate for the reduced effectiveness of insulin by secreting increased amounts of insulin (Polonsky, *Int. J. Obes. Relat. Metab. Disord.* 24 *Suppl* 2:529-31, 2000). The beta cells within the pancreatic islets initially compensate for insulin resistance by increasing insulin output. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the onset of Type 2 diabetes due to insufficient increases (or actual declines) in beta cell mass is apparently due to increased beta cell apoptosis relative to non-diabetic insulin resistant individuals (Butler et al., *Diabetes* 52:102-110, 2003).

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as syndrome X or Metabolic Syndrome. According to one widely used definition, a patient having Metabolic Syndrome is characterized as having three or more symptoms selected from the following group of five symptoms: (1) abdominal obesity, (2) hypertriglyceridemia, (3) low levels of high-density lipoprotein cholesterol (HDL), (4) high blood pressure, and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improves the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments have largely focused on three areas of pathophysiology: (1) hepatic glucose production (biguanides), (2) insulin resistance (PPAR agonists), (3) insulin secretion (sulfonylureas); (4) incretin hormone mimetics (GLP-1 derivatives and analogs, such as exenatide and luraglitide); and (5) inhibitors of incretin hormone degradation (DPP-4 inhibitors).

The biguanides belong to a class of drugs that are widely used to treat Type 2 diabetes. Phenformin and metformin are the two best known biguanides and do cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or insulin secretagogues, without increasing the risk of hypoglycemia. However, phenformin and metformin can induce lactic acidosis, nausea/vomiting, and diarrhea. Metformin has a lower risk of side effects than phenformin and is widely prescribed for the treatment of Type 2 diabetes.

The glitazones (e.g., 5-benzylthiazolidine-2,4-diones) are a class of compounds that can ameliorate hyperglycemia and other symptoms of Type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of Type 2 diabetes, resulting in partial or complete correction of elevated plasma glucose levels without the occurrence of hypoglycemia. PPAR-gamma agonism is believed to be responsible for the improved insulin sensititization that is observed in human patients who are treated with the glitazones. New PPAR agonists are currently being developed. Many of the newer PPAR compounds are agonists of one or more of the PPAR alpha, gamma and delta subtypes. The currently marketed PPAR gamma agonists are modestly effective in reducing plasma glucose and hemoglobin A1C. The currently marketed compounds do not greatly improve lipid metabolism and may actually have a negative effect on the lipid profile. Thus, the PPAR compounds represent an important advance in diabetic therapy.

Another widely used drug treatment involves the administration of insulin secretagogues, such as the sulfonylureas (e.g., tolbutamide, glipizide, and glimepiride). These drugs increase the plasma level of insulin by stimulating the pancreatic β-cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules, whereas other extracellular signals act as potentiators or inhibitors of insulin secretion through GPCR's present on the plasma membrane. Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

Dipeptidyl peptidase-IV (DPP-4) inhibitors (e.g., sitagliptin, vildagliptin, saxagliptin, and alogliptin) provide a new route to increase insulin secretion in response to food consumption. Glucagon-like peptide-1 (GLP-1) levels increase in response to the increases in glucose present after eating and glucagon stimulates the production of insulin. The serine proteinase enzyme DPP-4 which is present on many cell surfaces degrades GLP-1. DPP-4 inhibitors reduce degradation of GLP-1, thus potentiating its action and allowing for greater insulin production in response to increases in glucose through eating.

There has been a renewed focus on pancreatic islet-based insulin secretion that is controlled by glucose-dependent insulin secretion. This approach has the potential for stabilization and restoration of β-cell function. In this regard, the present application claims compounds that are antagonists of the somatostatin subtype receptor 3 (SSTR3) as a means to increase insulin secretion in response to rises in glucose resulting from eating a meal. These compounds may also be used as ligands for imaging (e.g., PET, SPECT) for assessment of beta cell mass and islet function. A decrease in β-cell mass can be determined with respect to a particular patient over the course of time.

U.S. Pat. No. 6,586,445 discloses β-carboline derivatives as somatostatin receptor antagonists and sodium channel blockers for treating numerous diseases, including diabetes. Related examples are imidazolyl tetrahydro-β-carboline derivatives based on the compounds provided in Poitout et al., *J. Med. Chem.* 44:2990-3000, 2001. U.S. Pat. No. 6,861,430 discloses β-carboline derivatives as SSTR3 antagonists for the treatment of depression, anxiety, and bipolar disorders. PCT application WO2009/011836 discloses β-carboline derivatives as SSTR3 antagonists for the treatment of diabetes. Decahydroisoquinoline derivatives that are selective SSTR3 antagonists are disclosed in Bänziger et al., *Tetrahedron:Assymetry* 14:3469-3477, 2003.

SUMMARY OF THE INVENTION

The present invention is directed to compounds of structural formula I, and pharmaceutically acceptable salts thereof:

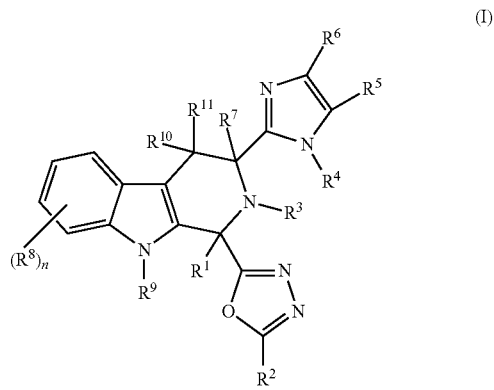

(I)

These bicyclic beta-carbolise derivatives are effective as antagonists of SSTR3. They are therefore useful for the treatment, control or prevention of disorders responsive to antagonism of SSTR3, such as Type 2 diabetes, insulin resistance, lipid disorders, obesity, atherosclerosis, Metabolic Syndrome, depression, and anxiety.

The present invention also relates to pharmaceutical compositions comprising the compounds of the present invention and a pharmaceutically acceptable carrier.

The present invention also relates to methods for the treatment, control, or prevention of disorders, diseases, or conditions responsive to antagonism of SSTR3 in a subject in need thereof by administering the compounds and pharmaceutical compositions of the present invention.

The present invention also relates to methods for the treatment, control, or prevention of Type 2 diabetes, hyperglycemia, insulin resistance, obesity, lipid disorders, atherosclerosis, and Metabolic Syndrome by administering the compounds and pharmaceutical compositions of the present invention.

The present invention also relates to methods for the treatment, control, or prevention of depression and anxiety by administering the compounds and pharmaceutical compositions of the present invention.

The present invention also relates to methods for the treatment, control, or prevention of obesity by administering the compounds of the present invention in combination with a therapeutically effective amount of another agent known to be useful to treat the condition.

The present invention also relates to methods for the treatment, control, or prevention of Type 2 diabetes by administering the compounds of the present invention in combination with a therapeutically effective amount of another agent known to be useful to treat the condition.

The present invention also relates to methods for the treatment, control, or prevention of atherosclerosis by administering the compounds of the present invention in combination with a therapeutically effective amount of another agent known to be useful to treat the condition.

The present invention also relates to methods for the treatment, control, or prevention of lipid disorders by administering the compounds of the present invention in combination with a therapeutically effective amount of another agent known to be useful to treat the condition.

The present invention also relates to methods for treating Metabolic Syndrome by administering the compounds of the present invention in combination with a therapeutically effective amount of another agent known to be useful to treat the condition.

The present invention also relates to methods for the treatment, control, or prevention of depression and anxiety by administering the compounds of the present invention in combination with a therapeutically effective amount of another agent known to be useful to treat the condition.

DETAILED DESCRIPTION OF THE INVENTION

The present invention is concerned with beta-carboline derivatives useful as antagonists of SSTR3. The compounds of the present invention are described by structural formula I:

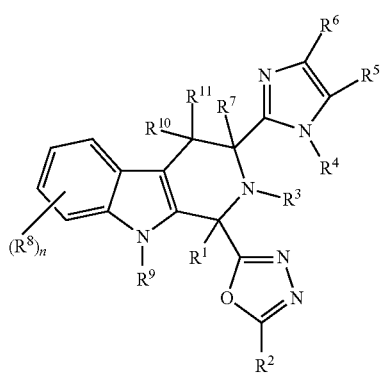

(I)

and pharmaceutically acceptable salts thereof, wherein:
$R^1$ is selected from the group consisting of:
(1) —$C_{1-6}$ alkyl-O—$C_{1-6}$ alkyl,
(2) —$C_{1-6}$ alkyl-O—$C_{1-6}$ alkyl-O—$C_{1-6}$ alkyl,
(3) —$C_{3-10}$ cycloalkyl, and
(4) —$C_{3-10}$ cycloheteroalkyl,
wherein alkyl, cycloalkyl and cycloheteroalkyl are unsubstituted or substituted with one to three substituents independently selected from $R^a$;
$R^2$ is selected from the group consisting of:
(1) —$C_{1-6}$ alkyl,
(2) —$C_{1-6}$ alkyl-O—$C_{1-6}$ alkyl,
(3) —$C_{3-7}$ cycloalkyl, and
(4) —$C_{3-6}$ cycloheteroalkyl,
wherein alkyl, cycloalkyl and cycloheteroalkyl are unsubstituted or substituted with one to three substituents independently selected from $R^f$;
$R^3$ is selected from the group consisting of:
(1) hydrogen, and
(2) $C_{1-10}$ alkyl, unsubstituted or substituted with one to five fluorines;
$R^4$ is selected from the group consisting of:
(1) hydrogen, and
(2) —$C_{1-8}$ alkyl, unsubstituted or substituted with one to five fluorines;
$R^5$ and $R^6$ are each independently selected from the group consisting of:
(1) hydrogen, and
(2) pyridine,
wherein pyridine is unsubstituted or substituted with one to three substituents independently selected from $R^i$, provided that one of $R^5$ and $R^6$ is pyridine and the other is hydrogen;
$R^7$ is selected from the group consisting of:
(1) hydrogen, and
(2) $C_{1-10}$ alkyl, unsubstituted or substituted with one to five fluorines;
each $R^8$ is independently selected from the group consisting of:
(1) hydrogen,
(2) —$NR^cS(O)_mR^e$,
(3) halogen,
(4) —$OCF_3$,
(5) —$OCHF_2$, and
(6) —$C_{1-10}$ alkyl, unsubstituted or substituted with one to five fluorines;
$R^9$ is selected from the group consisting of:
(1) hydrogen, and
(2) —$C_{1-10}$ alkyl, unsubstituted or substituted with one to five fluorines;
$R^{10}$ and $R^{11}$ are each independently selected from the group consisting of:
(1) hydrogen, and
(2) —$C_{1-4}$ alkyl, unsubstituted or substituted with one to five fluorines;
each $R^a$ is independently selected from the group consisting of:
(1) —$C_{1-6}$ alkyl,
(2) —$OC_{1-6}$ alkyl,
(3) —OH,
(4) —$NR^cS(O)_mR^e$,
(5) halogen,
(6) —$S(O)_mR^e$,
(7) —$S(O)_mNR^cR^d$,
(8) —$NR^cR^d$,
(9) —$C(O)R^e$,
(10) —$OC(O)R^e$,
(11) oxo,
(12) —$CO_2R^e$,
(13) —CN,
(14) —$C(O)NR^cR^d$,
(15) —$NR^cC(O)R^e$,
(16) —$NR^cC(O)OR^e$,
(17) —$NR^cC(O)NR^cR^d$,
(18) —$CF_3$,
(19) —$OCF_3$, and
(20) —$OCHF_2$;
$R^c$ and $R^d$ are each independently selected from the group consisting of:
(1) hydrogen,
(2) $C_{1-10}$ alkyl,
(3) $C_{2-10}$ alkenyl,
(4) $C_{3-6}$ cycloalkyl,
(5) $C_{3-6}$ cycloalkyl-$C_{1-10}$ alkyl-,
(6) $C_{3-10}$ cycloheteroalkyl,
(7) $C_{3-10}$ cycloheteroalkyl-$C_{1-10}$ alkyl-,
(8) aryl,
(9) heteroaryl,
(10) aryl-$C_{1-10}$ alkyl-, and
(11) heteroaryl-$C_{1-10}$ alkyl-,
wherein when $R^c$ and $R^d$ are not hydrogen, each $R^c$ and $R^d$ is unsubstituted or substituted with one to three substituents independently selected from $R^g$;
each $R^e$ is independently selected from the group consisting of:
(1) hydrogen,
(2) $C_{1-10}$ alkyl, (3) $C_{2-10}$ alkenyl,
(4) $C_{3-6}$ cycloalkyl,
(5) $C_{3-6}$ cycloalkyl-$C_{1-10}$ alkyl-,
(6) $C_{3-10}$ cycloheteroalkyl,
(7) $C_{3-10}$ cycloheteroalkyl-$C_{1-10}$ alkyl-,
(8) aryl,
(9) heteroaryl,
(10) aryl-$C_{1-10}$ alkyl-, and
(11) heteroaryl-$C_{1-10}$ alkyl-, wherein when $R^e$ is not hydrogen, each $R^e$ is unsubstituted or substituted with one to three substituents selected from $R^h$;

$R^f$ is selected from the group consisting of:
(1) halogen, and
(2) —$C_{1-10}$ alkyl, unsubstituted or substituted with one to five fluorines;

each $R^g$ is independently selected from the group consisting of:
(1) halogen,
(2) $C_{1-10}$ alkyl,
(3) —O—$C_{1-4}$ alkyl,
(4) —S(O)$_m$—$C_{1-4}$ alkyl,
(5) —CN,
(6) —$CF_3$,
(7) —$OCHF_2$, and
(8) —$OCF_3$;

each $R^h$ is independently selected from the group consisting of:
(1) halogen,
(2) $C_{1-10}$ alkyl,
(3) —O—$C_{1-4}$ alkyl,
(4) —S(O)$_m$—$C_{1-4}$ alkyl,
(5) —CN,
(6) —$CF_3$,
(7) —$OCHF_2$, and
(8) —$OCF_3$;

each $R^i$ is independently selected from the group consisting of:
(1) —$OR^e$,
(2) —$NR^c S(O)_m R^e$,
(3) halogen,
(4) —$S(O)_m R^e$,
(5) —$S(O)_m NR^c R^d$,
(6) —$NR^c R^d$,
(7) —$C(O)R^e$,
(8) —$OC(O)R^e$,
(9) oxo,
(10) —$CO_2 R^e$,
(11) —CN,
(12) —$C(O)NR^c R^d$,
(13) —$NR^c C(O)R^e$,
(14) —$NR^c C(O)OR^e$,
(15) —$NR^c C(O)NR^c R^d$,
(16) —$CF_3$,
(17) —$OCF_3$,
(18) —$OCHF_2$, and
(19) —$C_{1-10}$ alkyl;

n is 0, 1, 2, 3 or 4; and
m is 0, 1 or 2.

The invention has numerous embodiments, which are summarized below. The invention includes compounds of Formula I, which includes the compounds of formula Ia, Ib, Ic, Id, Ie and II. The invention also includes pharmaceutically acceptable salts of the compounds of formula I and pharmaceutical compositions comprising the compounds of formula I and a pharmaceutically acceptable carrier. The compounds of formula I are useful for the treatment of Type 2 diabetes, hyperglycemia, obesity, and lipid disorders that are associated with Type 2 diabetes.

In one embodiment of the present invention, $R^1$ is selected from the group consisting of: —$C_{1-6}$ alkyl-O—$C_{1-6}$ alkyl, —$C_{1-6}$ alkyl-O—$C_{1-6}$ alkyl-O—$C_{1-6}$ alkyl, —$C_{3-10}$ cycloalkyl, and —$C_{3-10}$ cycloheteroalkyl, wherein alkyl, cycloalkyl and cycloheteroalkyl are unsubstituted or substituted with one to three substituents independently selected from $R^a$. In a class of this embodiment, $R^1$ is selected from the group consisting of: —$C_{1-6}$ alkyl-O—$C_{1-6}$ alkyl, —$C_{1-6}$ alkyl-O—$C_{1-6}$ alkyl-β—$C_{1-6}$ alkyl, —$C_{3-10}$ cycloalkyl, and —$C_{3-10}$ cycloheteroalkyl, wherein alkyl, cycloalkyl and cycloheteroalkyl are unsubstituted or substituted with one to three substituents independently selected from $R^a$, and wherein cycloalkyl is substituted with one to three substituents independently selected from —$OR^e$. In a subclass of this class, $R^1$ is selected from the group consisting of: —$C_{1-6}$ alkyl-O—$C_{1-6}$ alkyl, —$C_{1-6}$ alkyl-O—$C_{1-6}$ alkyl-O—$C_{1-6}$ alkyl, —$C_{3-10}$ cycloalkyl, and —$C_{3-10}$ cycloheteroalkyl, wherein alkyl, cycloalkyl and cycloheteroalkyl are unsubstituted or substituted with one to three substituents independently selected from $R^a$, and wherein cycloalkyl is substituted with one to three substituents independently selected from —OH and —O—$C_{1-6}$ alkyl. In another class of this embodiment, $R^1$ is selected from the group consisting of —$C_{1-6}$ alkyl-O—$C_{1-6}$ alkyl, —$C_{1-6}$ alkyl-O—$C_{1-6}$ alkyl-O—$C_{1-6}$ alkyl, —$C_{3-10}$ cycloalkyl, and —$C_{3-10}$ cycloheteroalkyl, wherein alkyl, cycloalkyl and cycloheteroalkyl are unsubstituted or substituted with one to three substituents independently selected from $R^a$, and wherein cycloalkyl is substituted with one substituent independently selected from —$OR^e$. In a subclass of this class, $R^1$ is selected from the group consisting of: —$C_{1-6}$ alkyl-O—$C_{1-6}$ alkyl, —$C_{1-6}$ alkyl-O—$C_{1-6}$ alkyl-O—$C_{1-6}$ alkyl, —$C_{3-10}$ cycloalkyl, and —$C_{3-10}$ cycloheteroalkyl, wherein alkyl, cycloalkyl and cycloheteroalkyl are unsubstituted or substituted with one to three substituents independently selected from $R^a$, and wherein cycloalkyl is substituted with one substituent independently selected from —OH and —O—$C_{1-6}$ alkyl. In another class of this embodiment, $R^1$ is selected from the group consisting of —$C_{1-6}$ alkyl-O—$C_{1-6}$ alkyl, —$C_{1-6}$ alkyl-O—$C_{1-6}$ alkyl-O—$C_{1-6}$ alkyl, —$C_{3-10}$ cycloalkyl, and —$C_{3-10}$ cycloheteroalkyl, wherein alkyl, cycloalkyl and cycloheteroalkyl are unsubstituted or substituted with one to three substituents independently selected from $R^a$, and wherein cycloalkyl is substituted with one substituent independently selected from —O—$C_{1-6}$ alkyl.

In another class of this embodiment, $R^1$ is selected from the group consisting of: —$C_{1-6}$ alkyl-O—$C_{1-6}$ alkyl, —$C_{1-6}$ alkyl-O—$C_{1-6}$ alkyl-O—$C_{1-6}$ alkyl, —$C_{3-10}$ cycloalkyl, and —$C_{3-10}$ cycloheteroalkyl, wherein alkyl, cycloalkyl and cycloheteroalkyl are unsubstituted or substituted with one to two substituents independently selected from —OH and —O—$C_{1-6}$ alkyl; or a pharmaceutically acceptable salt thereof. In another class of this embodiment, $R^1$ is selected from the group consisting of: —$C_{1-6}$ alkyl-O—$C_{1-6}$ alkyl, —$C_{1-6}$ alkyl-O—$C_{1-6}$ alkyl-O—$C_{1-6}$ alkyl, —$C_{3-10}$ cycloalkyl, and —$C_{3-10}$ cycloheteroalkyl, wherein alkyl, cycloalkyl and cycloheteroalkyl are unsubstituted or substituted with one to two substituents independently selected from —O—$C_{1-6}$ alkyl; or a pharmaceutically acceptable salt thereof.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein alkyl, cyclobutyl, cyclohexyl, bicyclo[3.1.0]hexane, tetrahydropyran, and tetrahydrofuran are unsubstituted or substituted with one to three substituents independently selected from $R^a$. In a subclass of this class, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein alkyl, cyclobutyl, cyclohexyl, tetrahydropyran, and tetrahydrofuran are unsubstituted or substituted with one to three substituents independently selected from $R^a$.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein alkyl, cyclobutyl, cyclohexyl, bicyclo[3.1.0]hexane, tetrahydropyran, and tetrahydrofuran are unsubstituted or substituted with one to three substituents independently selected from $R^a$, and wherein cyclobutyl, cyclohexyl, and bicyclo[3.1.0]hexane are substituted with one substituent independently selected from —OH and —O—$C_{1-6}$ alkyl. In a subclass of this class, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein alkyl, cyclobutyl, cyclohexyl, tetrahydropyran, and tetrahydrofuran are unsubstituted or substituted with one to three substituents independently selected from $R^a$, and wherein cyclobutyl, and cyclohexyl are substituted with one substituent independently selected from —OH and —O—$C_{1-6}$ alkyl.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein alkyl, cyclobutyl, cyclohexyl, bicyclo[3.1.0]hexane, tetrahydropyran, and tetrahydrofuran are unsubstituted or substituted with one to three substituents independently selected from $R^a$, and wherein cyclobutyl, cyclohexyl and bicyclo[3.1.0]hexane are substituted with one substituent independently selected from —O—$C_{1-6}$ alkyl. In a subclass of this class, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein alkyl, cyclobutyl, cyclohexyl, tetrahydropyran, and tetrahydrofuran are unsubstituted or substituted with one to three substituents independently selected from $R^a$, and wherein cyclobutyl, and cyclohexyl are substituted with one substituent independently selected from —O—$C_{1-6}$ alkyl.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein cyclobutyl, cyclohexyl and bicyclo[3.1.0]hexane are substituted with one to three substituents independently selected from $R^a$. In a subclass of this class, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein cyclobutyl, and cyclohexyl are substituted with one to three substituents independently selected from $R^a$.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein cyclobutyl, cyclohexyl and bicyclo[3.1.0]hexane are substituted with one to three substituents independently selected from —OH and —O—$C_{1-6}$ alkyl. In a subclass of this class, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein cyclobutyl, and cyclohexyl are substituted with one to three substituents independently selected from —OH and —O—$C_{1-6}$ alkyl.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein cyclobutyl, cyclohexyl and bicyclo[3.1.0]hexane are substituted with one to three substituents independently selected from —O—$C_{1-6}$ alkyl. In a subclass of this class, $R^1$ is selected from the group consisting of —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein cyclobutyl, and cyclohexyl are substituted with one to three substituents independently selected from —O—$C_{1-6}$ alkyl.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein cyclobutyl, cyclohexyl and bicyclo[3.1.0]hexane are substituted with one substituent independently selected from $R^a$. In a subclass of this class, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein cyclobutyl, and cyclohexyl are substituted with one substituent independently selected from $R^a$.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein cyclobutyl, cyclohexyl and bicyclo[3.1.0]hexane are substituted with one substituent independently selected from —OH and —O—$C_{1-6}$ alkyl. In a subclass of this class, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein cyclobutyl, and cyclohexyl are substituted with one substituent independently selected from —OH and —O—$C_{1-6}$ alkyl.

In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein cyclobutyl, cyclohexyl and bicyclo[3.1.0]hexane are substituted with one substituent independently selected from —O—$C_{1-6}$ alkyl. In a subclass of this class, $R^1$ is selected from the group consisting of —$CH_2$—O—$CH_2CH_3$, —$CH_2$—O—$CH_2CD_3$, —$CH_2$—O—$CH_2CH_2$—O—$CH_3$, cyclobutyl, cyclohexyl, tetrahydropyran, and tetrahydrofuran, wherein cyclobutyl, and cyclohexyl are substituted with one substituent independently selected from —O—$C_{1-6}$ alkyl.

In another embodiment of the present invention, $R^1$ is selected from the group consisting of —$C_{1-6}$ alkyl-O—$C_{1-6}$ alkyl, —$C_{1-6}$ alkyl-O—$C_{1-6}$ alkyl-O—$C_{1-6}$ alkyl and —$C_{3-10}$ cycloheteroalkyl, wherein alkyl and cycloheteroalkyl are unsubstituted or substituted with one to three substituents independently selected from $R^a$. In a class of this embodiment, $R^1$ is selected from the group consisting of: —$C_{1-6}$ alkyl-O—$C_{1-6}$ alkyl, —$C_{1-6}$ alkyl-O—$C_{1-6}$ alkyl-O—$C_{1-6}$ alkyl and —$C_{3-10}$ cycloheteroalkyl, wherein alkyl and cycloheteroalkyl are unsubstituted or substituted with one to two substituents independently selected from —O—$C_{1-6}$ alkyl; or a pharmaceutically acceptable salt thereof. In another class of this embodiment, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, tetrahydropyran, and tetrahydrofuran, wherein alkyl, tetrahydropyran, and tetrahydrofuran are unsubstituted or substituted with one to three substituents independently selected from $R^a$.

In another class of this embodiment, $R^1$ is —$C_{1-6}$ alkyl-O—$C_{1-6}$ alkyl, wherein alkyl is unsubstituted or substituted with one to three substituents independently selected from $R^a$. In a subclass of this class, $R^1$ is selected from the group consisting of: —$CH_2$—O—$CH_2CH_3$, and —$CH_2$—O—$CH_2CD_3$, wherein alkyl is unsubstituted or substituted with one to three substituents independently selected from $R^a$. In another subclass of this class, $R^1$ is —$CH_2$—O—$CH_2CH_3$, wherein alkyl is unsubstituted or substituted with one to three substituents independently selected from $R^a$. In another class of this embodiment, $R^1$ is —$C_{1-6}$ alkyl-O—$C_{1-6}$ alkyl. In a subclass of this class, $R^1$ is selected from the group consisting of: —$CH_2$—O—$CH_2CH_3$, and —$CH_2$—O—$CH_2CD_3$. In another subclass of this class, $R^1$ is —$CH_2$—O—$CH_2CH_3$. In another subclass of this class, $R^1$ is —$CH_2$—O—$CH_2CD_3$.

In another class of this embodiment, $R^1$ is —$C_{1-6}$ alkyl-O—$C_{1-6}$ alkyl-O—$C_{1-6}$ alkyl, wherein alkyl is unsubstituted or substituted with one to two substituents independently selected from —O—$C_{1-6}$ alkyl; or a pharmaceutically acceptable salt thereof. In a subclass of this class, $R^1$ is —$CH_2$—O—$CH_2CH_2$—O—$CH_3$, wherein alkyl is unsubstituted or substituted with one to three substituents independently selected from $R^a$. In another class of this embodiment, $R^1$ is —$C_{1-6}$ alkyl-O—$C_{1-6}$ alkyl-O—$C_{1-6}$ alkyl. In a subclass of this class, $R^1$ is —$CH_2$—O—$CH_2CH_2$—O—$CH_3$.

In another class of this embodiment, $R^1$ is —$C_{3-10}$ cycloalkyl, wherein cycloalkyl is unsubstituted or substituted with one to three substituents independently selected from $R^a$. In a subclass of this class, $R^1$ is selected from: cyclobutyl, cyclohexyl and bicyclo[3.1.0]hexane, wherein cyclobutyl, cyclohexyl and bicyclo[3.1.0]hexane are =substituted or substituted with one to three substituents independently selected from $R^a$. In another subclass of this class, $R^1$ is selected from: cyclobutyl, and cyclohexyl, wherein cyclobutyl, and cyclohexyl are unsubstituted or substituted with one to three substituents independently selected from $R^a$. In another subclass of this class, $R^1$ is cyclobutyl or cyclohexyl.

In another class of this embodiment, $R^1$ is —$C_{3-10}$ cycloalkyl, wherein cycloalkyl is unsubstituted or substituted with one to three substituents independently selected from $R^a$, and wherein cycloalkyl is substituted with one substituent selected from —OH and —$OC_{1-6}$ alkyl. In a subclass of this class, $R^1$ is selected from: cyclobutyl, cyclohexyl and bicyclo[3.1.0]hexane, wherein cyclobutyl, cyclohexyl and bicyclo[3.1.0]hexane are unsubstituted or substituted with one to three substituents independently selected from $R^a$, and wherein cyclobutyl, cyclohexyl and bicyclo[3.1.0]hexane are substituted with one substituent selected from —OH and —$OC_{1-6}$ alkyl. In another subclass of this class, $R^1$ is selected from: cyclobutyl, and cyclohexyl, wherein cyclobutyl, and cyclohexyl are unsubstituted or substituted with one to three substituents independently selected from $R^a$, and wherein cyclobutyl, and cyclohexyl are substituted with one substituent selected from —OH and —$OC_{1-6}$ alkyl.

In another class of this embodiment, $R^1$ is —$C_{3-10}$ cycloheteroalkyl, wherein cycloheteroalkyl is unsubstituted or substituted with one to three substituents independently selected from $R^a$. In a subclass of this class, $R^1$ is selected from tetrahydropyran and tetrahydrofuran, wherein tetrahydropyran and tetrahydrofuran are unsubstituted or substituted with one to three substituents independently selected from $R^a$.

In another embodiment of the present invention, $R^2$ is selected from the group consisting of: —$C_{1-6}$ alkyl, —$C_{1-6}$ alkyl-O—$C_{1-6}$ alkyl, —$C_{3-7}$ cycloalkyl, and —$C_{3-6}$ cycloheteroalkyl, wherein alkyl, cycloalkyl and cycloheteroalkyl are unsubstituted or substituted with one to three substituents independently selected from $R^f$.

In another embodiment of the present invention, $R^2$ is selected from the group consisting of: —$C_{1-6}$ alkyl, —$C_{1-6}$ alkyl-O—$C_{1-6}$ alkyl, and —$C_{3-6}$ cycloheteroalkyl, wherein alkyl and cycloheteroalkyl are unsubstituted or substituted with one to three substituents independently selected from $R^f$. In a class of this embodiment, $R^2$ is selected from the group consisting of —$CH_3$, —$C(CH_3)_3$, —$CH(CH_3)_2$, —$CH_2CH_2$—O—$CH_3$, tetrahydropyran, and tetrahydrofuran, wherein alkyl, tetrahydropyran, and tetrahydrofuran are unsubstituted or substituted with one to three substituents independently selected from $R^f$.

In another embodiment of the present invention, $R^2$ is —$C_{1-6}$ alkyl, wherein alkyl is unsubstituted or substituted with one to three substituents independently selected from $R^f$. In a class of this embodiment, $R^2$ is selected from the group consisting of: —$CH_3$, —$C(CH_3)_3$, and —$CH(CH_3)_2$, wherein alkyl is unsubstituted or substituted with one to three substituents independently selected from $R^f$.

In another embodiment of the present invention, $R^2$ is —$C_{1-6}$ alkyl. In a class of this embodiment, $R^2$ is selected from the group consisting of: —$CH_3$, —$C(CH_3)_3$, and —$CH(CH_3)_2$.

In another embodiment of the present invention, $R^2$ is —$C_{1-6}$ alkyl-O—$C_{1-6}$ alkyl, wherein alkyl is unsubstituted or substituted with one to three substituents independently selected from $R^f$. In a class of this embodiment, $R^2$ is —$CH_2CH_2$—O—$CH_3$, wherein alkyl is unsubstituted or substituted with one to three substituents independently selected from $R^f$. In another class of this embodiment of the present invention, $R^2$ is —$CH_2CH_2$—O—$CH_3$.

In another embodiment of the present invention, $R^2$ is —$C_{3-6}$ cycloheteroalkyl, wherein cycloheteroalkyl is unsubstituted or substituted with one to three substituents independently selected from $R^f$. In a class of this embodiment, $R^2$ is selected from the group consisting of: tetrahydropyran and tetrahydrofuran, wherein tetrahydropyran and tetrahydrofuran are unsubstituted or substituted with one to three substituents independently selected from $R^f$. In another class of this embodiment, $R^2$ is selected from the group consisting of: tetrahydropyran, and tetrahydrofuran.

In another embodiment of the present invention, $R^3$ is selected from the group consisting of: hydrogen and —$C_{1-10}$ alkyl, wherein alkyl is unsubstituted or substituted with one to five fluorines. In a class of this embodiment, $R^3$ is hydrogen. In another class of this embodiment, $R^3$ is —$C_{1-6}$ alkyl, wherein alkyl is unsubstituted or substituted with one to five fluorines. In another class of this embodiment, $R^3$ is —$C_{1-6}$ alkyl.

In another embodiment of the present invention, $R^4$ is selected from the group consisting of: hydrogen and —$C_{1-8}$ alkyl, wherein alkyl is unsubstituted or substituted with one to five fluorines. In a class of this embodiment, $R^4$ is hydrogen. In another class of this embodiment, $R^4$ is —$C_{1-6}$ alkyl, wherein alkyl is unsubstituted or substituted with one to five fluorines. In another class of this embodiment, $R^4$ is —$C_{1-6}$ alkyl.

In another embodiment of the present invention, $R^5$ and $R^6$ are each independently selected from the group consisting of: hydrogen, and pyridine, wherein pyridine is unsubstituted or substituted with one to three substituents independently selected from $R^1$, provided that one of $R^5$ and $R^6$ is pyridine and the other is hydrogen.

In another embodiment of the present invention, $R^5$ is independently selected from the group consisting of: hydrogen, and pyridine, wherein pyridine is unsubstituted or substituted with one to three substituents independently selected from $R^i$, provided that one of $R^5$ and $R^6$ is pyridine and the other is hydrogen. In a class of this embodiment, $R^5$ is pyridine, wherein pyridine is unsubstituted or substituted with one or two substituents independently selected from $R^i$. In another class of this embodiment, $R^5$ is hydrogen.

In another embodiment of the present invention, $R^6$ is independently selected from the group consisting of: hydrogen, and pyridine, wherein pyridine is unsubstituted or substituted with one to three substituents independently selected from $R^i$, provided that one of $R^5$ and $R^6$ is pyridine and the other is hydrogen. In a class of this embodiment, $R^6$ is pyridine, wherein pyridine is unsubstituted or substituted with one or two substituents independently selected from $R^i$. In another class of this embodiment, $R^6$ is hydrogen.

In another embodiment of the present invention, $R^6$ is pyridine, wherein pyridine is unsubstituted or substituted with one, two or three substituents independently selected from $R^i$. In a class of this embodiment, $R^6$ is pyridine, wherein pyridine is unsubstituted or substituted with one or two substituents independently selected from $R^i$. In another class of this embodiment, $R^6$ is pyridine, wherein pyridine is unsubstituted or substituted with two substituents independently selected from $R^i$. In another class of this embodiment, $R^6$ is pyridine, wherein pyridine is substituted with two substituents independently selected from $R^i$. In another class of this embodiment, $R^6$ is pyridine, wherein pyridine is unsubstituted or substituted with one substituent independently selected from $R^i$. In another class of this embodiment, $R^6$ is pyridine, wherein pyridine is substituted with one substituent independently selected from $R^i$. In another class of this embodiment, $R^6$ is pyridin-2-yl, wherein pyridine is unsubstituted or substituted with one, two or three substituents independently selected from $R^i$. In another class of this embodiment, $R^6$ is pyridin-2-yl, wherein pyridine is unsubstituted or substituted with one or two substituents independently selected from $R^i$. In another class of this embodiment, $R^6$ is pyridin-2-yl, wherein pyridine is unsubstituted or substituted with two substituents independently selected from $R^i$. In another class of this embodiment, $R^6$ is pyridin-2-yl, wherein pyridine is substituted with two substituents independently selected from $R^i$. In another class of this embodiment, $R^6$ is pyridin-2-yl, wherein pyridine is unsubstituted or substituted with one substituent independently selected from $R^i$. In another class of this embodiment, $R^6$ is pyridin-2-yl, wherein pyridine is substituted with one substituent independently selected from $R^i$.

In another class of this embodiment, $R^6$ is pyridin-2-yl, wherein pyridine is unsubstituted or substituted with one, two or three substituents independently selected from halogen and $C_{1-6}$alkyl. In another class of this embodiment, $R^6$ is pyridin-2-yl, wherein pyridine is unsubstituted or substituted with one or two substituents independently selected from halogen and $C_{1-6}$alkyl. In another class of this embodiment, $R^6$ is pyridin-2-yl, wherein pyridine is unsubstituted or substituted with two substituents independently selected from halogen and $C_{1-6}$alkyl. In another class of this embodiment, $R^6$ is pyridin-2-yl, wherein pyridine is substituted with two substituents independently selected from halogen and $C_{1-6}$alkyl. In another class of this embodiment, $R^6$ is pyridin-2-yl, wherein pyridine is unsubstituted or substituted with one substituent independently selected from halogen and $C_{1-6}$alkyl. In another class of this embodiment, $R^6$ is pyridin-2-yl, wherein pyridine is substituted with one substituent independently selected from halogen and $C_{1-6}$alkyl. In another class of this embodiment, $R^6$ is pyridin-2-yl, wherein pyridine is substituted with one substituent independently selected from halogen. In another class of this embodiment, $R^6$ is pyridin-2-yl, wherein pyridine is substituted with one substituent independently selected from $C_{1-6}$alkyl.

In another class of this embodiment, $R^6$ is pyridin-2-yl, wherein pyridine is unsubstituted or substituted with one, two or three substituents independently selected from fluoro and —$CH_3$. In another class of this embodiment, $R^6$ is pyridin-2-yl, wherein pyridine is unsubstituted or substituted with one or two substituents independently selected from fluoro and —$CH_3$. In another class of this embodiment, $R^6$ is pyridin-2-yl, wherein pyridine is unsubstituted or substituted with two substituents independently selected from fluoro and —$CH_3$. In another class of this embodiment, $R^6$ is pyridin-2-yl, wherein pyridine is substituted with two substituents independently selected from fluoro and —$CH_3$. In another class of this embodiment, $R^6$ is pyridin-2-yl, wherein pyridine is substituted with a fluoro and a —$CH_3$ substituent. In another class of this embodiment, $R^6$ is pyridin-2-yl, wherein pyridine is unsubstituted or substituted with one substituent independently selected from fluoro and —$CH_3$. In another class of this embodiment, $R^6$ is pyridin-2-yl, wherein pyridine is substituted with one substituent independently selected from fluoro and —$CH_3$. In another class of this embodiment, $R^6$ is pyridin-2-yl, wherein pyridine is substituted with fluoro. In another class of this embodiment, $R^6$ is pyridin-2-yl, wherein pyridine is substituted with —$CH_3$.

In another embodiment of the present invention, $R^6$ is selected from the group consisting of: 5-fluoro-pyridin-2-yl, and 5-fluoro-6-methyl-pyridin-2-yl; or a pharmaceutically acceptable salt thereof. In a class of this embodiment, $R^6$ is 5-fluoro-pyridin-2-yl; or a pharmaceutically acceptable salt thereof. In another class of this embodiment, $R^6$ is 5-fluoro-6-methyl-pyridin-2-yl; or a pharmaceutically acceptable salt thereof.

In another embodiment of the present invention, $R^7$ is selected from the group consisting of: hydrogen and —$C_{1-10}$ alkyl, wherein alkyl is unsubstituted or substituted with one to five fluorines. In a class of this embodiment, $R^7$ is hydrogen. In another class of this embodiment, $R^7$ is —$C_{1-6}$ alkyl, wherein alkyl is unsubstituted or substituted with one to five fluorines. In another class of this embodiment, $R^7$ is —$C_{1-6}$ alkyl.

In another embodiment of the present invention, each $R^8$ is independently selected from the group consisting of: hydrogen, —$NR^cS(O)_mR^e$, halogen, —$OCF_3$, —$OCHF_2$, and —$C_{1-10}$ alkyl, wherein alkyl is unsubstituted or substituted with one to five fluorines. In a class of this embodiment, each $R^8$ is independently selected from the group consisting of: hydrogen and halogen. In another class of this embodiment, $R^8$ is hydrogen. In another class of this embodiment, $R^8$ is halogen.

In another embodiment of the present invention, $R^9$ is selected from the group consisting of: hydrogen and $C_{1-10}$ alkyl, wherein alkyl is unsubstituted or substituted with one to three substituents independently selected from $R^a$. In a class of this embodiment, $R^9$ is hydrogen. In another class of this embodiment, $R^9$ is $—C_{1-10}$ alkyl, wherein alkyl is unsubstituted or substituted with one to three substituents independently selected from $R^a$. In another class of this embodiment, $R^9$ is $—C_{1-10}$ alkyl.

In another embodiment of the present invention, $R^{10}$ and $R^{11}$ are independently selected from the group consisting of hydrogen and $—C_{1-4}$ alkyl, wherein alkyl is unsubstituted or substituted with one to five fluorines. In a class of this embodiment, $R^{10}$ and $R^{11}$ are hydrogen. In another class of this embodiment, $R^{10}$ and $R^{11}$ are $—C_{1-4}$ alkyl, wherein alkyl is unsubstituted or substituted with one to five fluorines. In another class of this embodiment, $R^{10}$ and $R^{11}$ are $—C_{1-4}$ alkyl.

In another embodiment of the present invention, $R^{10}$ is independently selected from the group consisting of hydrogen and $—C_{1-4}$ alkyl, wherein alkyl is unsubstituted or substituted with one to five fluorines. In a class of this embodiment, $R^{10}$ is hydrogen. In another class of this embodiment, $R^{10}$ is $—C_{1-4}$ alkyl, wherein alkyl is unsubstituted or substituted with one to five fluorines. In another class of this embodiment, $R^{10}$ is $—C_{1-4}$ alkyl.

In another embodiment of the present invention, $R^{11}$ is independently selected from the group consisting of: hydrogen, and $—C_{1-4}$ alkyl, wherein alkyl is unsubstituted or substituted with one to five fluorines. In a class of this embodiment, $R^{11}$ is hydrogen. In another class of this embodiment, $R^{11}$ is $—C_{1-4}$ alkyl, wherein alkyl is unsubstituted or substituted with one to five fluorines. In another class of this embodiment, $R^{11}$ is $—C_{1-4}$ alkyl.

In another embodiment of the present invention, each $R^a$ is independently selected from the group consisting of: $—C_{1-6}$ alkyl, $—OC_{1-6}$ alkyl, $—OH$, $—NR^cS(O)_mR^e$, halogen, $—S(O)_mR^e$, $—S(O)_mNR^cR^d$, $—NR^cR^d$, $—C(O)R^e$, $—OC(O)R^e$, oxo, $—CO_2R^e$, $—CN$, $—C(O)NR^cR^d$, $—NR^cC(O)R^e$, $—NR^cC(O)OR^e$, $—NR^cC(O)NR^cR^d$, $—CF_3$, $—OCF_3$, and $—OCHF_2$. In a class of this embodiment, each $R^a$ is independently selected from the group consisting of: $—OC_{1-6}$ alkyl, $—OH$, $—NR^cS(O)_mR^e$, halogen, $—S(O)_mR^e$, $—S(O)_mNR^cR^d$, $—NR^cR^d$, $—C(O)R^e$, $—OC(O)R^e$, oxo, $—CO_2R^e$, $—CN$, $—C(O)NR^cR^d$, $—NR^cC(O)R^e$, $—NR^cC(O)OR^e$, $—NR^cC(O)NR^cR^d$, $—CF_3$, $—OCF_3$, and $—OCHF_2$. In another class of this embodiment, each $R^a$ is independently selected from the group consisting of: $—C_{1-6}$ alkyl, $—OC_{1-6}$ alkyl, and halogen. In another class of this embodiment, each $R^a$ is independently selected from the group consisting of: $—OC_{1-6}$ alkyl, and halogen. In another class of this embodiment, $R^a$ is $—OC_{1-6}$ alkyl. In another class of this embodiment, $R^a$ is -halogen. In another class of this embodiment, $R^a$ is $—C_{1-6}$ alkyl.

In another embodiment of the present invention, $R^c$ and $R^d$ are each independently selected from the group consisting of: hydrogen, $—C_{1-10}$ alkyl, $—C_{2-10}$ alkenyl, $—C_{3-6}$ cycloalkyl, $C_{3-6}$ cycloalkyl-$C_{1-10}$ alkyl-, $—C_{3-10}$ cycloheteroalkyl, $C_{3-10}$ cycloheteroalkyl-$C_{1-10}$ alkyl-, aryl, heteroaryl, aryl-$C_{1-10}$ alkyl-, and heteroaryl-$C_{1-10}$ alkyl-, wherein when $R^c$ and $R^d$ are not hydrogen, each $R^c$ and $R^d$ is unsubstituted or substituted with one to three substituents independently selected from $R^g$. In a class of this embodiment, $R^c$ and $R^d$ are each independently selected from the group consisting of: hydrogen, and $—C_{1-6}$ alkyl, wherein alkyl is unsubstituted or substituted with one to three substituents independently selected from $R^g$. In another class of this embodiment, $R^c$ and $R^d$ are each independently selected from the group consisting of: hydrogen, and $—C_{1-6}$ alkyl. In another class of this embodiment, $R^c$ and $R^d$ are each hydrogen. In another class of this embodiment, $R^c$ and $R^d$ are each $—C_{1-6}$ alkyl, wherein alkyl is unsubstituted or substituted with one to three substituents independently selected from $R^g$. In another class of this embodiment, $R^c$ and $R^d$ are each $—C_{1-6}$ alkyl.

In another embodiment of the present invention, $R^c$ is independently selected from the group consisting of: hydrogen, $—C_{1-10}$ alkyl, $—C_{2-10}$ alkenyl, $—C_{3-6}$ cycloalkyl, $C_{3-6}$ cycloalkyl-$C_{1-10}$ alkyl-, $—C_{3-10}$ cycloheteroalkyl, $C_{3-10}$ cycloheteroalkyl-$C_{1-10}$ alkyl-, aryl, heteroaryl, aryl-$C_{1-10}$ alkyl-, and heteroaryl-$C_{1-10}$ alkyl-, wherein when $R^c$ is not hydrogen, each $R^c$ is unsubstituted or substituted with one to three substituents independently selected from $R^g$. In a class of this embodiment, $R^c$ is independently selected from the group consisting of: hydrogen, and $—C_{1-6}$ alkyl, wherein alkyl is unsubstituted or substituted with one to three substituents independently selected from $R^g$. In another class of this embodiment, $R^c$ is independently selected from the group consisting of: hydrogen, and $—C_{1-6}$ alkyl. In another class of this embodiment, $R^c$ is hydrogen. In another class of this embodiment, $R^c$ is $—C_{1-6}$ alkyl, wherein alkyl is unsubstituted or substituted with one to three substituents independently selected from $R^g$. In another class of this embodiment, $R^c$ is $—C_{1-6}$ alkyl.

In another embodiment of the present invention, $R^d$ is independently selected from the group consisting of hydrogen, $—C_{1-10}$ alkyl, $—C_{2-10}$ alkenyl, $—C_{3-6}$ cycloalkyl, $C_{3-6}$ cycloalkyl-$C_{1-10}$ alkyl-, $—C_{3-10}$ cycloheteroalkyl, $C_{3-10}$ cycloheteroalkyl-$C_{1-10}$ alkyl-, aryl, heteroaryl, aryl-$C_{1-10}$ alkyl-, and heteroaryl-$C_{1-10}$ alkyl-, wherein when $R^d$ is not hydrogen, each $R^d$ is unsubstituted or substituted with one to three substituents independently selected from $R^g$. In a class of this embodiment, $R^d$ is independently selected from the group consisting of: hydrogen, and $—C_{1-6}$ alkyl, wherein alkyl is unsubstituted or substituted with one to three substituents independently selected from $R^g$. In another class of this embodiment, $R^d$ is independently selected from the group consisting of: hydrogen, and $—C_{1-6}$ alkyl. In another class of this embodiment, $R^d$ is hydrogen. In another class of this embodiment, $R^d$ is $—C_{1-6}$ alkyl, wherein alkyl is unsubstituted or substituted with one to three substituents independently selected from $R^g$. In another class of this embodiment, $R^d$ is $—C_{1-6}$ alkyl.

In another embodiment of the present invention, each $R^e$ is independently selected from the group consisting of: hydrogen, $—C_{1-10}$ alkyl, $—C_{2-10}$ alkenyl, $—C_{3-6}$ cycloalkyl, $C_{3-6}$ cycloalkyl-$C_{1-10}$ alkyl-, $—C_{3-10}$ cycloheteroalkyl, $C_{3-10}$ cycloheteroalkyl-$C_{1-10}$ alkyl-, aryl, heteroaryl, aryl-$C_{1-10}$ alkyl-, and heteroaryl-$C_{1-10}$ alkyl-, wherein when $R^e$ is not hydrogen, each $R^e$ is unsubstituted or substituted with one to three substituents selected from $R^h$. In a class of this embodiment, each $R^e$ is independently selected from the group consisting of: hydrogen, and $—C_{1-6}$ alkyl, wherein alkyl is unsubstituted or substituted with one to three substituents selected from $R^h$. In another class of this embodiment, each $R^e$ is independently selected from the group consisting of: hydrogen, and $—C_{1-6}$ alkyl. In another class of this embodiment, $R^e$ is hydrogen. In another class of this embodiment, $R^e$ is $—C_{1-6}$ alkyl, wherein alkyl is unsubstituted or substituted with one to three substituents selected from $R^h$. In another class of this embodiment, $R^e$ is $—C_{1-6}$ alkyl.

In another embodiment of the present invention, $R^f$ is selected from the group consisting of: halogen, and $—C_{1-10}$ alkyl, wherein alkyl is unsubstituted or substituted with one to five fluorines. In a class of this embodiment, $R^f$ is selected from: Br, F, Cl and $—CH_3$, wherein $—CH_3$ is unsubstituted or substituted with one to five fluorines. In another class of this embodiment, $R^f$ is selected from: F, Cl and $—CH_3$. In another class of this embodiment, $R^f$ is selected from: F and $—CH_3$. In another class of this embodiment, $R^f$ is halogen. In a subclass of this class, $R^f$ is selected from F, Br, and Cl. In another subclass of this class, $R^f$ is F. In another class of this embodiment, $R^f$ is —$C_{1-10}$ alkyl, wherein alkyl is unsubstituted or substituted with one to five fluorines. In another class of this embodiment, $R^f$ is —$C_{1-6}$ alkyl. In another class of this embodiment, $R^f$ is —$CH_3$.

In another embodiment of the present invention, each $R^g$ is independently selected from the group consisting of halogen, —$C_{1-10}$ alkyl, —O—$C_{1-4}$ alkyl, —S(O)$_m$—$C_{1-4}$ alkyl, —CN, —$CF_3$, —$OCHF_2$, and —$OCF_3$. In a class of this embodiment, each $R^g$ is independently selected from the group consisting of halogen, and —$C_{1-6}$ alkyl. In another class of this embodiment, $R^g$ is halogen. In another class of this embodiment, $R^g$ is —$C_{1-6}$ alkyl.

In another embodiment of the present invention, each $R^h$ is independently selected from the group consisting of: halogen, —$C_{1-10}$ alkyl, —O—$C_{1-4}$ alkyl, —S(O)$_m$—$C_{1-4}$ alkyl, —CN, —$CF_3$, —$OCHF_2$, and —$OCF_3$. In a class of this embodiment, each $R^h$ is independently selected from the group consisting of: halogen, and —$C_{1-6}$ alkyl. In another class of this embodiment, $R^h$ is halogen. In another class of this embodiment, $R^h$ is —$C_{1-6}$ alkyl.

In another embodiment of the present invention, each $R^i$ is independently selected from the group consisting of: —$OR^e$, —$NR^cS(O)_mR^e$, halogen, —S(O)$_m R^e$, —S(O)$_m NR^cR^d$, —$NR^cR^d$, C(O)$R^e$, —OC(O)$R^e$, oxo, —$CO_2R^e$, —CN, —C(O)$NR^cR^d$, —$NR^cC(O)R^e$, —$NR^cC(O)OR^e$, —$NR^cC(O)NR^cR^d$, —$CF_3$, —$OCF_3$, —$OCHF_2$, and —$C_{1-10}$ alkyl.

In another embodiment of the present invention, each $R^i$ is independently selected from the group consisting of: halogen, and —$C_{1-6}$alkyl. In a class of this embodiment, each $R^i$ is independently selected from the group consisting of: F, Br, Cl and —$CH_3$. In another class of this embodiment, each $R^i$ is independently selected from the group consisting of: F and —$CH_3$. In another class of this embodiment, each $R^i$ is independently selected from the group consisting of: halogen. In a subclass of this class, $R^i$ is independently selected from the group consisting of: Br, Cl and F. In another subclass of this class, $R^i$ is Cl or F. In another subclass of this class, $R^i$ is F. In another class of this embodiment, $R^i$ is —$C_{1-6}$alkyl. In a subclass of this class, $R^i$ is —$CH_3$.

In another embodiment of the present invention, m is 0, 1, or 2. In a class of this embodiment, m is 1 or 2. In another class of this embodiment, m is 0 or 2. In another class of this embodiment, m is 0 or 1. In another class of this embodiment, m is 0. In another class of this embodiment, m is 1. In another class of this embodiment, m is 2.

In another embodiment of the present invention, n is 0, 1, 2, 3 or 4. In a class of this embodiment, n is 0, 1 or 2. In another class of this embodiment, n is 0 or 1. In another class of this embodiment, n is 1 or 2. In another class of this embodiment, n is 0 or 2. In another class of this embodiment, n is 0. In another class of this embodiment, n is 1. In another class of this embodiment, n is 2. In another class of this embodiment, n is 3. In another class of this embodiment, n is 4.

In another embodiment of the present invention, there are provided compounds of formula I and II wherein: $R^3$, $R^4$, $R^5$, $R^7$, $R^8$, $R^9$, $R^{10}$, and $R^{11}$ are each hydrogen; or a pharmaceutically acceptable salt thereof.

In another embodiment of the present invention, there are provided compounds of formula I and II wherein: $R^a$ is —$OC_{1-6}$ alkyl; $R^f$ is —$C_{1-6}$ alkyl; and each $R^i$ is independently selected from the group consisting of: halogen and —$C_{1-6}$alkyl; or a pharmaceutically acceptable salt thereof.

In another embodiment of the present invention, there are provided compounds of formula I and II wherein: $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein alkyl, cyclobutyl, cyclohexyl, bicyclo[3.1.0]hexane, tetrahydropyran, and tetrahydrofuran are unsubstituted or substituted with one to three substituents independently selected from $R^a$; $R^3$, $R^4$, $R^5$, $R^7$, $R^8$, $R^9$, $R^{10}$, and $R^{11}$ are each hydrogen; $R^6$ is pyridin-2-yl, wherein pyridine is unsubstituted or substituted with one or two substituents independently selected from $R^1$; and $R^2$ is independently selected from the group consisting of: —$C_{1-6}$ alkyl, —$C_{1-6}$ alkyl-O—$C_{1-6}$ alkyl, and —$C_{3-6}$ cycloheteroalkyl, wherein alkyl and cycloheteroalkyl are unsubstituted or substituted with one to three substituents independently selected from $R^f$; or a pharmaceutically acceptable salt thereof.

In another embodiment of the present invention, there are provided compounds of formula I and II wherein: $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein alkyl, cyclobutyl, cyclohexyl, bicyclo[3.1.0]hexane, tetrahydropyran, and tetrahydrofuran are unsubstituted or substituted with one substituent independently selected from $R^a$; $R^3$, $R^4$, $R^5$, $R^7$, $R^8$, $R^9$, $R^{10}$, and $R^{11}$ are each hydrogen; $R^6$ is pyridin-2-yl, wherein pyridine is unsubstituted or substituted with one or two substituents independently selected from $R^i$; and $R^2$ is independently selected from the group consisting of: —$C_{1-6}$ alkyl, —$C_{1-6}$ alkyl-O—$C_{1-6}$ alkyl, and —$C_{3-6}$ cycloheteroalkyl, wherein alkyl and cycloheteroalkyl are unsubstituted or substituted with one substituent independently selected from $R^f$; or a pharmaceutically acceptable salt thereof.

In another embodiment of the present invention, $R^1$ is selected from the group consisting of: —$CH_2$—O—$CH_2CH_3$, —$CH_2$—O—$CH_2CD_3$, —$CH_2$—O—$CH_2CH_2$—O—$CH_3$, cyclobutyl, cyclohexyl, bicyclo[3.1.0]hexane, tetrahydropyran, and tetrahydrofuran, wherein alkyl, cyclobutyl, cyclohexyl, bicyclo[3.1.0]hexane, tetrahydropyran, and tetrahydrofuran are unsubstituted or substituted with one to three substituents independently selected from $R^a$; $R^3$, $R^4$, $R^5$, $R^7$, $R^8$, $R^9$, $R^{10}$, and $R^{11}$ are each hydrogen; $R^6$ is pyridin-2-yl, wherein pyridine is unsubstituted or substituted with one or two substituents independently selected from $R^i$; and $R^2$ is selected from the group consisting of: —$CH_3$, —$C(CH_3)_3$, —$CH(CH_3)_2$, —$CH_2CH_2$—O—$CH_3$, tetrahydropyran, and tetrahydrofuran, wherein alkyl, tetrahydropyran, and tetrahydrofuran are unsubstituted or substituted with one to three substituents independently selected from $R^f$; or a pharmaceutically acceptable salt thereof.

In another embodiment of the present invention, there are provided compounds of formula I and II wherein: $R^1$ is —$C_{1-6}$ alkyl-O—$C_{1-6}$ alkyl, wherein alkyl is unsubstituted or substituted with one to three substituents independently selected from $R^a$; $R^6$ is pyridin-2-yl, wherein pyridine is unsubstituted or substituted with one or two substituents independently selected from halogen and $C_{1-6}$alkyl; and $R^2$ is —$C_{1-6}$ alkyl, wherein alkyl is unsubstituted or substituted with one to three substituents independently selected from $R^f$; or a pharmaceutically acceptable salt thereof.

In another embodiment of the present invention, there are provided compounds of formula I and II wherein: $R^1$ is —$C_{1-6}$ alkyl-O—$C_{1-6}$ alkyl; $R^6$ is pyridin-2-yl, wherein pyridine is unsubstituted or substituted with one or two substituents independently selected from halogen and $C_{1-6}$ alkyl; and $R^2$ is —$C_{1-6}$ alkyl; or a pharmaceutically acceptable salt thereof.

In another embodiment of the present invention, there are provided compounds of formula I and II wherein: $R^1$ is —$C_{1-6}$ alkyl-O—$C_{1-6}$ alkyl; $R^6$ is pyridin-2-yl, wherein pyridine is unsubstituted or substituted with one or two substituents independently selected from fluoro and —$CH_3$; and $R^2$ is —$CH_3$; or a pharmaceutically acceptable salt thereof.

In another embodiment of the present invention, there are provided compounds of structural formula II having the indicated R stereochemical configuration at the stereogenic carbon atom marked with an *:

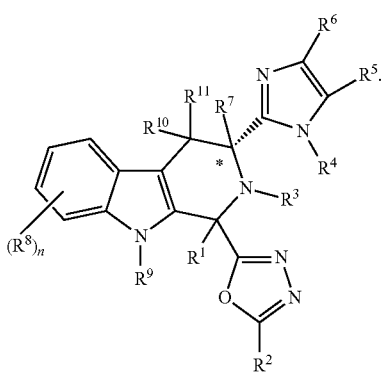

(II)

In another embodiment of the present invention, the invention relates to compounds of

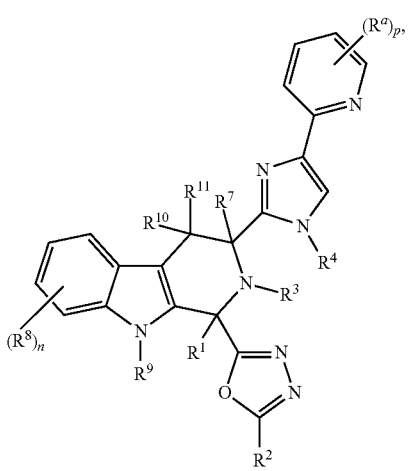

(Ia)

or pharmaceutically acceptable salts thereof.

In another embodiment of the present invention, the invention relates to compounds of structural formula Ib:

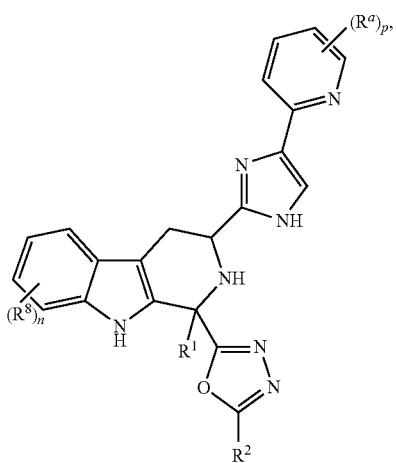

(Ib)

or pharmaceutically acceptable salts thereof.

In another embodiment of the present invention, the invention relates to compounds of structural formula Ic:

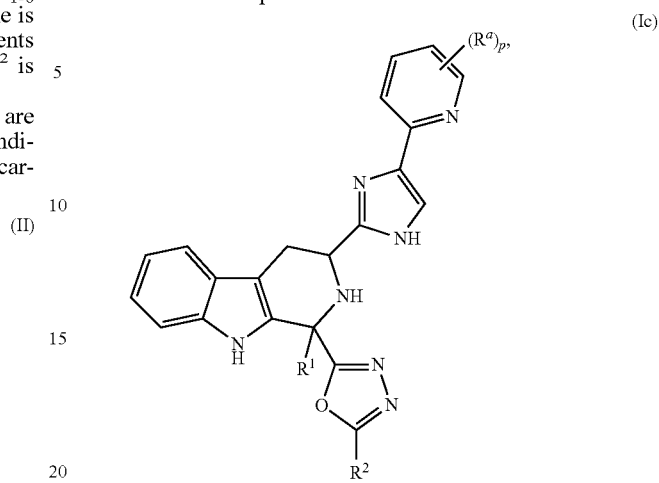

(Ic)

or pharmaceutically acceptable salts thereof.

In another embodiment of the present invention, the invention relates to compounds of structural formula Id:

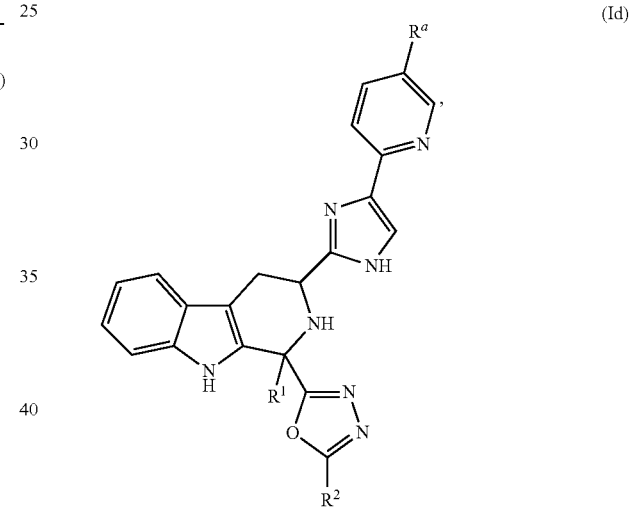

(Id)

or pharmaceutically acceptable salts thereof.

In another embodiment of the present invention, the invention relates to compounds of structural formula Ie:

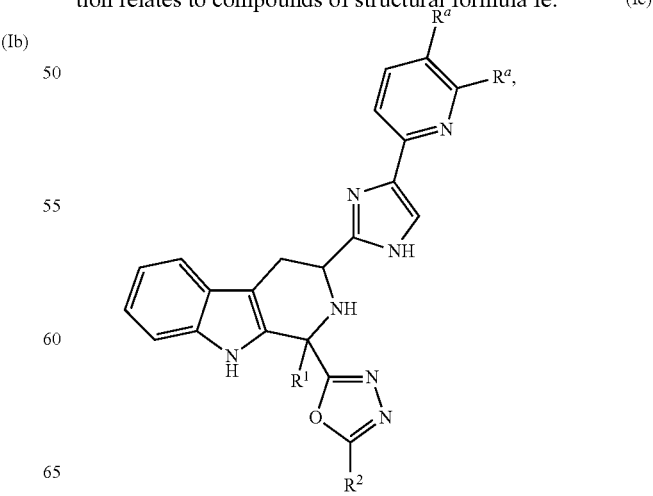

(Ie)

or pharmaceutically acceptable salts thereof.

Illustrative, but nonlimiting examples, of the compounds of the present invention that are useful as antagonists of SSTR3 are the following beta-carbolines:
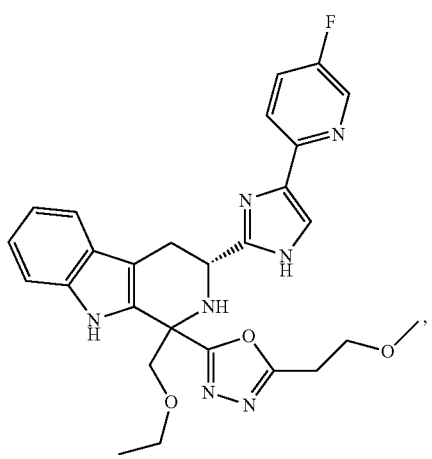
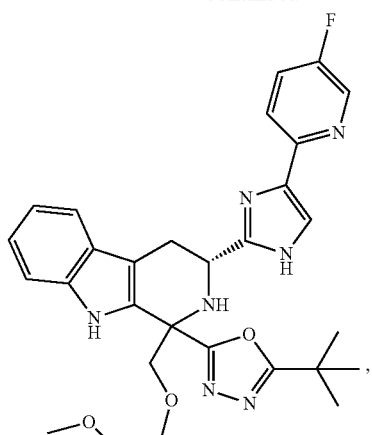
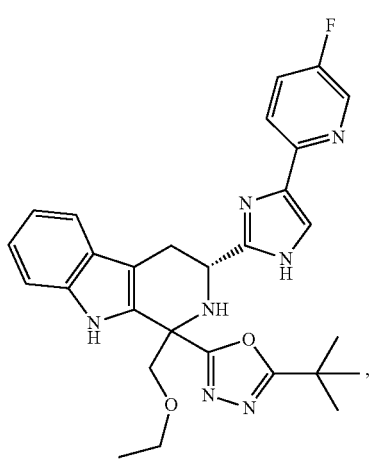
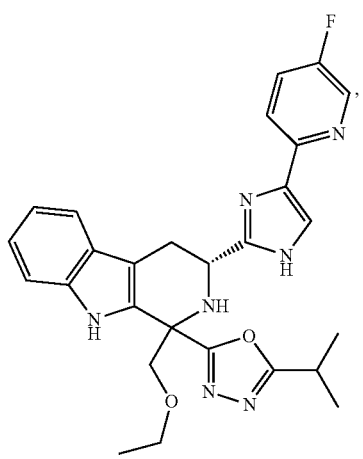
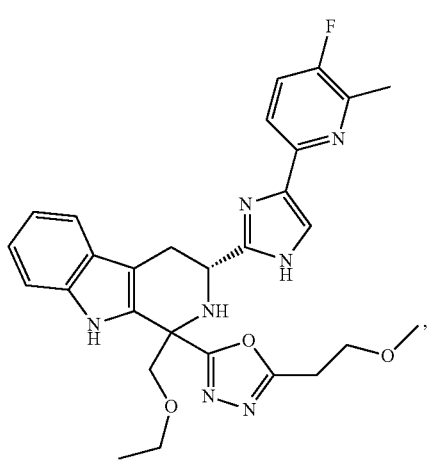
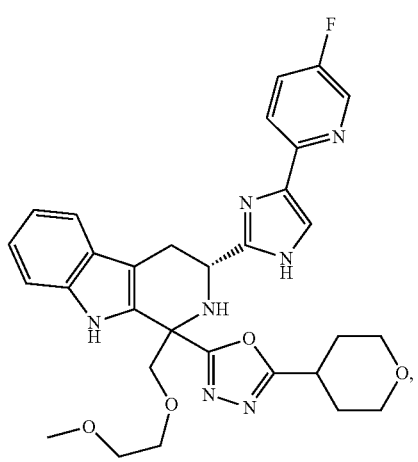

23
-continued
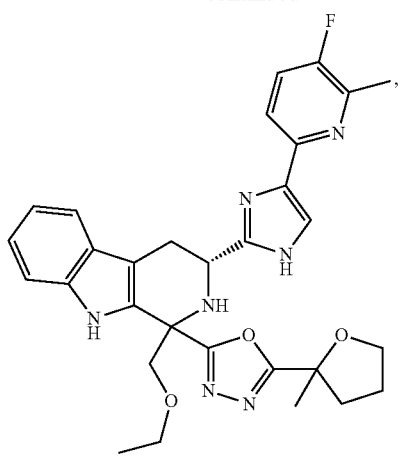
24
-continued
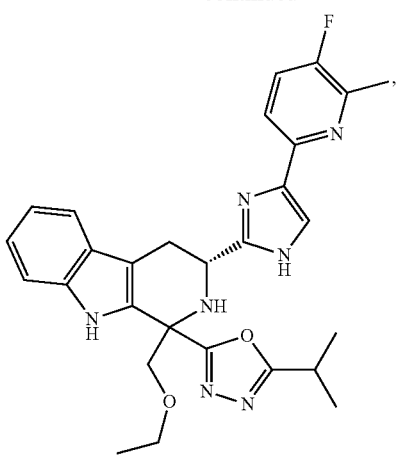
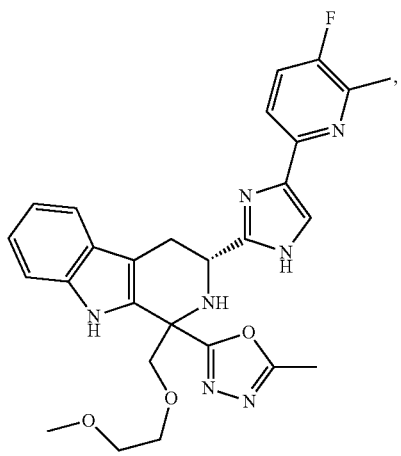
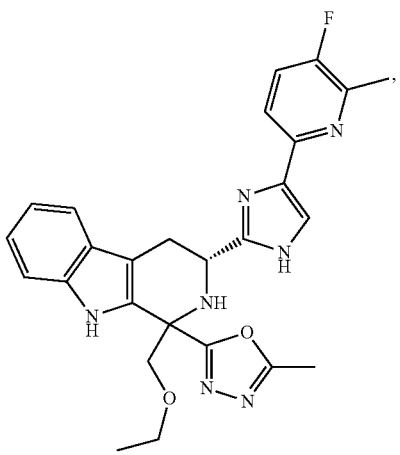
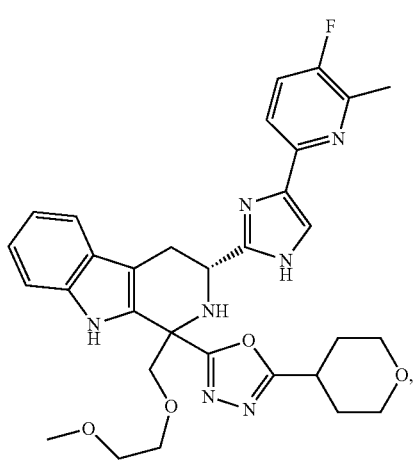
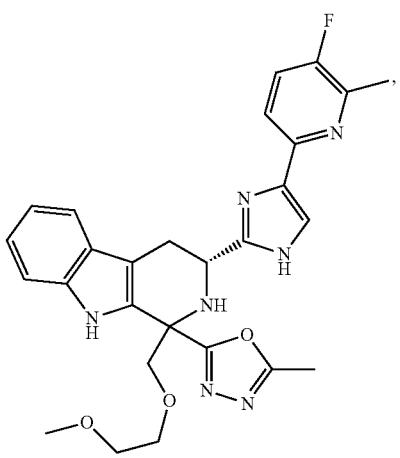

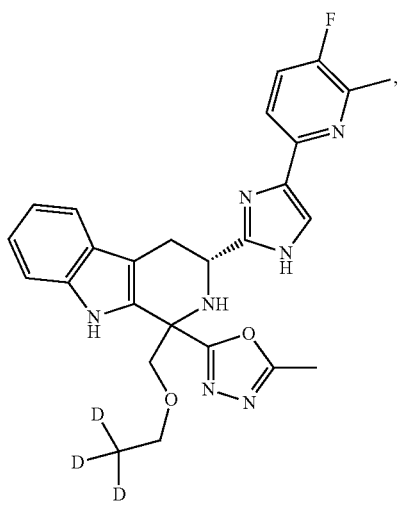
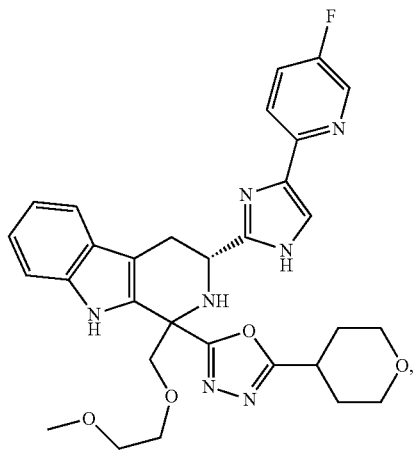
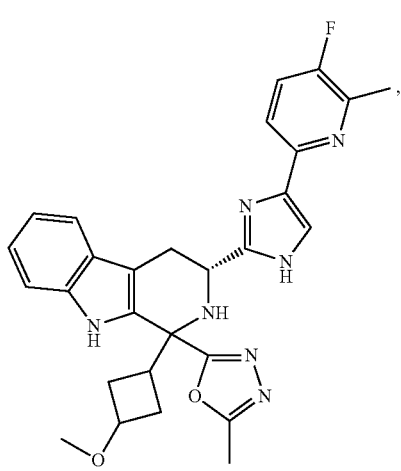
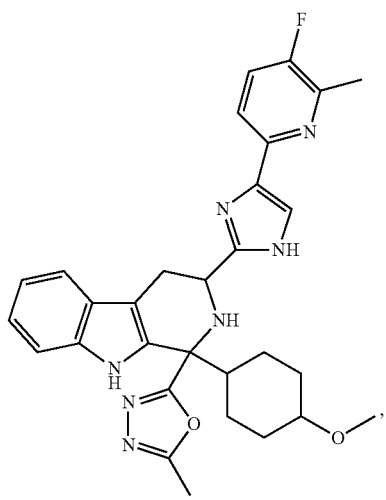
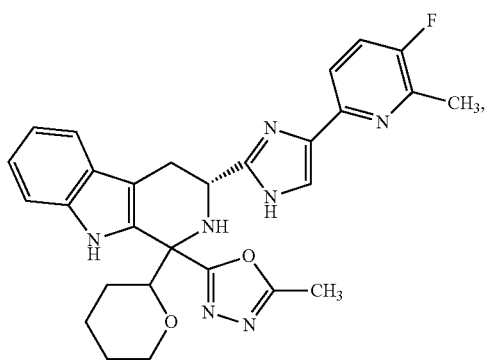
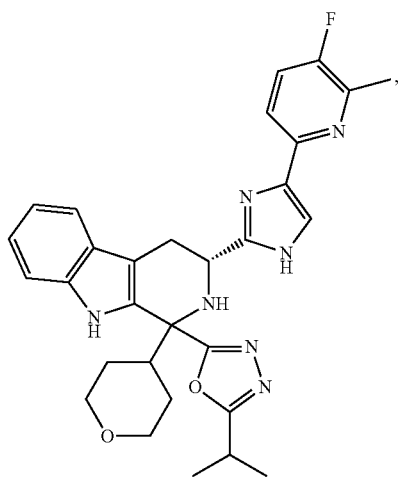

-continued

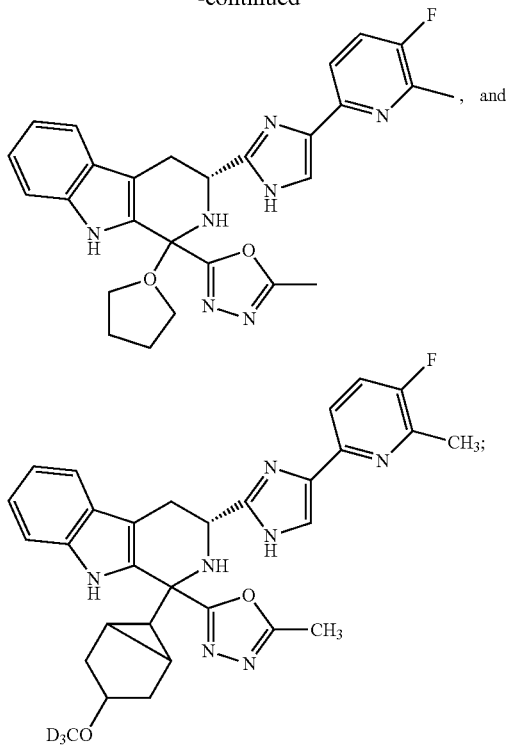

, and and pharmaceutically acceptable salts thereof.

The SSTR3 as identified herein is a target for affecting insulin secretion and assessing beta-cell mass. Glucose stimulated insulin secretion was found to be stimulated by abrogating the expression of SSTR3 and through the use of an SSTR3 selective antagonist. An important physiological action of insulin is to decrease blood glucose levels. As disclosed in the present application, targeting the SSTR3 has different uses including therapeutic applications, diagnostic applications, and evaluation of potential therapeutics.

Somatostatin is a hormone that exerts a wide spectrum of biological effects mediated by a family of seven transmembrane (TM) domain G-protein-coupled receptors. (Lahlou et al., Ann. N.Y. Acad. Sci. 1014:121-131, 2004, Reisine et al., Endocrine Review 16:427-442, 1995.) The predominant active forms of somatostatin are somatostatin-14 and somatostatin-28. Somatostatin-14 is a cyclic tetradecapeptide. Somatostatin-28 is an extended form of somatostatin-14.

Somatostatin subtype receptor 3 (SSTR3) is the third, of five, related G-protein receptor subtypes responding to somatostatin. The other receptors are the somatostatin subtype receptor 1 (SSTR1), somatostatin subtype receptor 2 (SSTR2), somatostatin subtype receptor 4 (SSTR4) and somatostatin subtype receptor 5 (SSTR5). The five distinct subtypes are encoded by separate genes segregated on different chromosomes. (Patel et al., Neuroendocrinol. 20:157-198, 1999.) All five receptor subtypes bind somatostatin-14 and somatostatin-28, with low nanomolar affinity. The ligand binding domain for somatostatin is made up of residues in TMs III-VII with a potential contribution by the second extracellular loop. Somatostatin receptors are widely expressed in many tissues, frequently as multiple subtypes that coexist in the same cell.

The five different somatostatin receptors all functionally couple to inhibition of adenylate cyclase by a pertussin-toxin sensitive protein ($G_{\alpha i1-3}$). (Lahlou et al., Ann. N.Y. Acad. Sci. 1014:121-131, 2004.) Somatostatin-induced inhibition of peptide secretion results mainly from a decrease in intracellular $Ca^{2+}$.

Among the wide spectrum of somatostatin effects, several biological responses have been identified with different receptor subtypes selectivity. These include growth hormone (GH) secretion mediated by SSTR2 and SSTR5, insulin secretion mediated by SSTR1 and SSTR5, glucagon secretion mediated by SSTR2, and immune responses mediated by SSTR2. (Patel et al., Neuroendocrinol. 20:157-198, 1999; Crider et al., Expert Opin. Ther. Patents 13:1427-1441, 2003.)

Different somatostatin receptor sequences from different organisms are well known in the art. (See for example, Reisine et al., Endocrine Review 16:427-442, 1995.) Human, rat, and murine SSTR3 sequences and encoding nucleic acid sequences are provided in SEQ ID NO: 3 (human SSTR3 cDNA gi|44890055|ref|NM_001051.2| CDS 526.1782); SEQ ID NO: 4 (human SSTR3 AA gi|4557861|ref|NP_001042.1|); SEQ ID NO: 5 (mouse SSTR3 cDNA gi|6678040|ref|NM_009218.1| CDS1.1287); SEQ ID NO: 6 (mouse SSTR3 AA gi|6678041|ref|NP_033244.1|); SEQ ID NO: 7 (rat SSTR3 cDNA gi|19424167|ref|NM_133522.1| CDS 656.1942); SEQ ID NO: 8 (rat SSTR3 A gi|19424168|ref|NP_598206.1|).

SSTR3 antagonists can be identified using SSTR3 and nucleic acid encoding for SSTR3. Suitable assays include detecting compounds competing with a SSTR3 agonist for binding to SSTR3 and determining the functional effect of compounds on a SSTR3 cellular or physiologically relevant activity. SSTR3 cellular activities include cAMP phospholipase C increase, tyrosine phosphatases increase, endothelial nitric oxide synthase (eNOS) decrease, $K^+$ channel increase, $Na^+/H^+$ exchange decrease, and ERK decrease. (Lahlou et al., Ann. N.Y. Acad. Sci. 1014:121-131, 2004.) Functional activity can be determined using cell lines expressing SSTR3 and determining the effect of a compound on one or more SSTR3 activities (e.g., Poitout et al., J. Med. Chem. 44:2900-3000, 2001; Hocart et al., J. Med. Chem. 41:1146-1154, 1998).

SSTR3 binding assays can be performed by labeling somatostatin and determining the ability of a compound to inhibit somatostatin binding. (Poitout et al., J. Med. Chem. 44:29900-3000, 2001; Hocart et al., J. Med. Chem. 41:1146-1154, 1998.) Additional formats for measuring binding of a compound to a receptor are well-known in the art.

A physiologically relevant activity for SSTR3 inhibition is stimulating insulin secretion. Stimulation of insulin secretion can be evaluated in vitro or in vivo.

SSTR3 antagonists can be identified experimentally or based on available information. A variety of different SSTR3 antagonists are well known in the art. Examples of such antagonists include peptide antagonists, β-carboline derivatives, and a decahydroisoquinoline derivative. (Poitout et al., J. Med. Chem. 44:29900-3000, 2001, Hocart et al., J. Med. Chem. 41:1146-1154, 1998, Reubi et al., PNAS 97:13973-13978, 2000, Bänziger et al., Tetrahedron: Assymetry 14:3469-3477, 2003, Crider et al., Expert Open. Ther. Patents 13:1427-1441, 2003, Troxler et al., International Publication No. WO 02/081471, International Publication Date Oct. 17, 2002).

Antagonists can be characterized based on their ability to bind to SSTR3 (Ki) and effect SSTR3 activity ($IC_{50}$), and to selectively bind to SSTR3 and selectively affect SSTR3 activity. Preferred antagonists strongly and selectively bind to SSTR3 and inhibit SSTR3 activity.

In different embodiments concerning SSTR3 binding, the antagonist has a Ki (nM) less than 600, preferably less than 100, more preferably less than 50, even more preferably less than 25 or even more preferably less than 10. Ki can be measured as described by Poitout et al., *J. Med. Chem.* 44:29900-3000, 2001 and described herein.

A selective SSTR3 antagonist binds SSTR3 at least 10 times stronger than it binds SSTR1, SSTR2, SSTR4, and SSTR5. In different embodiments concerning selective SSTR3 binding, the antagonist binds to each of SSTR1, SSTR2, SSTR4, and SSTR5 with a Ki greater than 1000, or preferably greater than 2000 nM and/or binds SSTR3 at least 40 times, more preferably at least 100 times, or more preferably at least 500 times, greater than it binds to SSTR1, SSTR2, SSTR4, and SSTR5.

In different embodiments concerning SSTR3 activity, the antagonist has an $IC_{50}$ (nM) less than 600, preferably less than 100, more preferably less than 50, or more preferably less than 10 nM. $IC_{50}$ can be determined by measuring inhibition of somatostatin-14 induced reduction of cAMP accumulation due to forskolin (1 μM) in CHO-K1 cells expressing SSTR3, as described by Poitout et al., *J. Med. Chem.* 44:29900-3000, 2001.

Preferred antagonists have a preferred or more preferred Ki, a preferred or more preferred 1050, and a preferred or more preferred selectivity. More preferred antagonists have a Ki (nM) less than 25; are at least 100 times selective for SSTR3 compared to SSTR1, SSTR2, SSTR4 and SSTR5; and have a $IC_{50}$ (nM) less than 50.

The β-carboline compounds of the present invention wherein the oxadiazole ring system is substituted with a $R^2$ substitutent have been found to have much lower affinity for sodium, as well as other ion channels, and thus are more selective antagonists of SSTR3. This selectivity is expected to reduce potential cardiovascular and other side effects of the compounds of the present invention.

The combination of the ether side chain, oxadiazole, and substituted pyridine in structural formulas (I) and (II) have the unexpected benefit of an increased binding potency (lower Ki and/or lower $IC_{50}$) for the human SSTR3 receptor relative to compounds with alternative substituents. Additionally, the compounds of structural formulas (I) and (II) in which R1 is a linear or cyclic ether, or wherein R1 is substituted with an ether or alkoxy substituent, have the unexpected benefit of significantly diminished potency on the hERG potassium ion channel. This lower potency for hERG channel blockade, as evidenced by a decrease in MK-499 binding relative to the SSTR3 receptor, reduces the potential for prolongation of the QT interval which is associated with causing the sometimes fatal ventricular arrhythmia known as torsades de pointes. For discussions of the correlation between hERG channel blockade and ventricular arrythmias, see the following recent reviews: M. R. Bowiby et al., *Curr. Drug Metab.* 9:965-970 (2008); A. Lagrutta et al., *Curr. Topics Med. Chem.* 8:1102-1112 (2008); A. Dennis et al., *Biochem. Soc. Trans.* 35:1060-1063 (2007); and M. Recanatini et al., *Med. Res. Rev.* 25:133-166 (2005). The compounds of formulas (I) and (II) have the unexpected benefits of greater selectivity for activities associated with the SSTR3 receptor (>10,000-fold selective) and wider safety margins with respect to potentially fatal arrythmias.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means an aromatic or partially aromatic heterocycle that contains at least one ring heteroatom selected from O, S and N. "Heteroaryl" thus includes heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridyl (pyridinyl), oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, 1,3-benzodioxolyl, benzo-1,4-dioxanyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Cycloheteroalkyl" means mono- or bicyclic or bridged saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "cycloheteroalkyl" include tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). The term also includes bridged rings such as 5-azabicyclo[2.2.1]heptyl, 2,5-diazabicyclo [2.2.1]heptyl, 2-azabicyclo[2.2.1]heptyl, 7-azabicyclo[2.2.1] heptyl, 2,5-diazabicyclo[2.2.2]octyl, 2-azabicyclo[2.2.2]octyl, and 3-azabicyclo[3.2.2]nonyl, and azabicyclo[2.2.1] heptanyl. The cycloheteroalkyl ring may be substituted on the ring carbons and/or the ring nitrogens.

"Halogen" includes fluorine, chlorine, bromine and iodine.

By "oxo" is meant the functional group "=O" which is an oxygen atom connected to the molecule via a double bond, such as, for example, (1) "C=(O)", that is a carbonyl group;

(2) "S=(O)", that is, a sulfoxide group; and (3) "N=(O)", that is, an N-oxide group, such as pyridyl-N-oxide.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

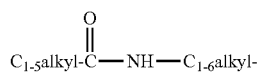

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Alternatively, any stereoisomer or isomers of a compound of the general structural formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of the present invention. Examples of tautomers which are intended to be encompassed within the compounds of the present invention are illustrated below:

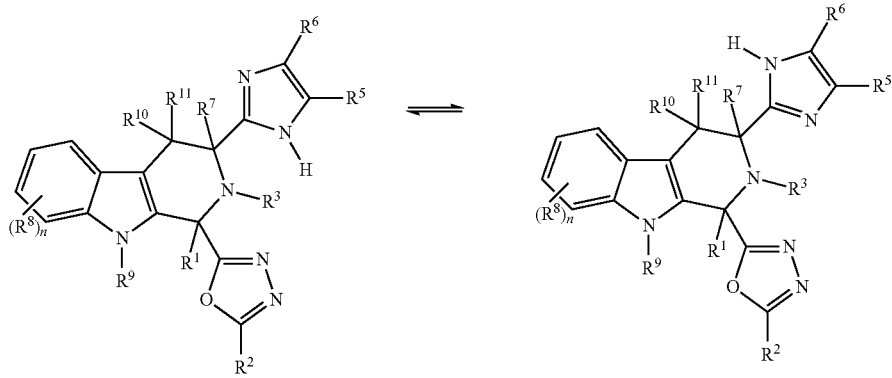

Optical Isomers—Diastereoisomers—Geometric Isomers—Tautomers:

Compounds of structural formula I may contain one or more asymmetric centers and can thus occur as racemates and racemic mixtures, single enantiomers, diastereoisomeric mixtures and individual diastereoisomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

In the compounds of structural formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H) and deuterium ($^2$H, also denoted as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Salts:

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, including but not limited to the ethyl acetate solvate, and in particular, the hydrates of the compounds of structural formula I are included in the present invention as well.

Exemplifying the invention is the use of the compounds disclosed in the Examples and herein.

Utilities:

The compounds described herein are potent and selective antagonists of the somatostatin subtype receptor 3 (SSTR3). The compounds are efficacious in the treatment of diseases that are modulated by SSTR3 ligands, which are generally antagonists. Many of these diseases are summarized below.

One or more of the following diseases may be treated by the administration of a therapeutically effective amount of a compound of Formula I, or a pharmaceutically acceptable salt thereof, to a patient in need of treatment. Also, the compounds of Formula I may be used for the manufacture of a medicament for treating one or more of these diseases:

(1) non-insulin dependent diabetes mellitus (Type 2 diabetes);
(2) hyperglycemia;
(3) Metabolic Syndrome;
(4) obesity;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) hyperapoBlipoproteinemia; and
(11) atherosclerosis.

One embodiment of the uses of the compounds is directed to the treatment of one or more of the following diseases by administering a therapeutically effective amount to a patient in need of treatment. The compounds may be used for manufacturing a medicament for use in the treatment of one or more of these diseases:

(1) Type 2 diabetes;
(2) hyperglycemia;
(3) Metabolic Syndrome;
(4) obesity; and
(5) hypercholesterolemia.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, and medicaments as described herein may also be effective in reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds may also be effective in delaying or preventing vascular restenosis and diabetic retinopathy.

The compounds of this invention may also have utility in improving or restoring β-cell function, so that they may be useful in treating type 1 diabetes or in delaying or preventing a patient with Type 2 diabetes from needing insulin therapy.

The compounds generally may be efficacious in treating one or more of the following diseases: (1) Type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure (hypertension), and (19) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of: hypercholesterolemia, atherosclerosis, hyperlipidemia, hypertriglyceridemia, dyslipidemia, high LDL, and low HDL.

Administration and Dose Ranges:

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 500 milligrams. For a particularly potent compound, the dosage for an adult human may be as low as 0.1 mg. In some cases, the daily dose may be as high as one gm. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 25 mg, 50 mg, 100 mg, 200 mg, 300 mg, 400 mg, 500 mg, and 750 mg. Other oral forms may also have the same or similar dosages.

Pharmaceutical Compositions:

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and unsubstituted or other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions as oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

In some instances, depending on the solubility of the compound or salt being administered, it may be advantageous to formulate the compound or salt as a solution in an oil such as a triglyceride of one or more medium chain fatty acids, a lipophilic solvent such as triacetin, a hydrophilic solvent (e.g.

propylene glycol), or a mixture of two or more of these, also unsubstituted or including one or more ionic or nonionic surfactants, such as sodium lauryl sulfate, polysorbate 80, polyethoxylated triglycerides, and mono and/or diglycerides of one or more medium chain fatty acids. Solutions containing surfactants (especially 2 or more surfactants) will form emulsions or microemulsions on contact with water. The compound may also be formulated in a water soluble polymer in which it has been dispersed as an amorphous phase by such methods as hot melt extrusion and spray drying, such polymers including hydroxylpropylmethylcellulose acetate (HPMCAS), hydroxylpropylmethyl cellulose (HPMCS), and polyvinylpyrrolidinones, including the homopolymer and copolymers.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant or mixture of surfactants such as hydroxypropylcellulose, polysorbate 80, and mono and diglycerides of medium and long chain fatty acids. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy:

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPAR agonists, when the patient's glycemic levels are not adequately responding to treatment.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides, such as metformin and phenformin;

(c) protein tyrosine phosphatase-1B (PIP-1B) inhibitors;

(d) dipeptidyl peptidase-IV (DPP-4) inhibitors, such as sitagliptin, saxagliptin, vildagliptin, and alogliptin;

(e) insulin or insulin mimetics;

(f) sulfonylureas such as tolbutamide, glimepiride, glipizide, and related materials;

(g) $\alpha$-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPAR$\alpha$ agonists, such as fenofibric acid derivatives (gemfibrozil, clofibrate, fenofibrate and bezafibrate), (v) cholesterol absorption inhibitors, such as ezetimibe, (vi) acyl CoA:cholesterol acyltransferase (ACAT) inhibitors, such as avasimibe, (vii) CETP inhibitors, such as torcetrapib, and (viii) phenolic antioxidants, such as probucol;

(i) PPAR$\alpha$/$\gamma$ dual agonists, such as muraglitazar, tesaglitazar, farglitazar, and JT-501;

(j) PPAR$\delta$ agonists, such as those disclosed in WO97/28149;

(k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and $\beta_3$ adrenergic receptor agonists;

(l) ileal bile acid transporter inhibitors;

(m) agents intended for use in inflammatory conditions, such as aspirin, non-steroidal anti-inflammatory drugs, glucocorticoids, azulfidine, and cyclooxygenase-2 (Cox-2) selective inhibitors;

(n) glucagon receptor antagonists;

(O) GLP-1;

(p) GIP-1;

(q) GLP-1 analogs and derivatives, such as exendins, (e.g., exenatide and liruglatide), and (r) 11$\beta$-hydroxysteroid dehydrogenase-1 (HSD-1) inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DPP-4 inhibitors, and cannabinoid receptor 1 (CB1) inverse agonists/antagonists.

BIOLOGICAL ASSAYS

Somatostatin Subtype Receptor 3 Production

SSTR3 can be produced using techniques well known in the art including those involving chemical synthesis and those involving recombinant production. (See e.g., Vincent, *Peptide and Protein Drug Delivery*, New York, N.Y., Decker, 1990; *Current Protocols in Molecular Biology*, John Wiley, 1987-2002, and Sambrook et al., *Molecular Cloning, A Laboratory Manual*, $2^{nd}$ Edition, Cold Spring Harbor Laboratory Press, 1989.)

Recombinant nucleic acid techniques for producing a protein involve introducing, or producing, a recombinant gene encoding the protein in a cell and expressing the protein. A purified protein can be obtained from cell. Alternatively, the activity of the protein in a cell or cell extract can be evaluated.

A recombinant gene contains nucleic acid encoding a protein along with regulatory elements for protein expression. The recombinant gene can be present in a cellular genome or can be part of an expression vector.

The regulatory elements that may be present as part of a recombinant gene include those naturally associated with the protein encoding sequence and exogenous regulatory elements not naturally associated with the protein encoding sequence. Exogenous regulatory elements such as an exogenous promoter can be useful for expressing a recombinant gene in a particular host or increasing the level of expression. Generally, the regulatory elements that are present in a recombinant gene include a transcriptional promoter, a ribosome binding site, a terminator, and an unsubstituted or present operator. A preferred element for processing in eukaryotic cells is a polyadenylation signal.

Expression of a recombinant gene in a cell is facilitated through the use of an expression vector. Preferably, an expression vector in addition to a recombinant gene also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

If desired, expression in a particular host can be enhanced through codon optimization. Codon optimization includes use of more preferred codons. Techniques for codon optimization in different hosts are well known in the art.

Enhancement of Glucose Dependent Insulin Secretion (GDIS) by SSTR3 Antagonists in Isolated Mouse Islet Cells:

Pancreatic islets of Langerhans were isolated from the pancreas of normal C57BL/6J mice (Jackson Laboratory, Maine) by collagenase digestion and discontinuous Ficoll gradient separation, a modification of the original method of Lacy and Kostianovsky (Lacy et al., *Diabetes* 16:35-39, 1967). The islets were cultured overnight in RPMI 1640 medium (11 mM glucose) before GDIS assay.

To measure GDIS, islets were first preincubated for 30 minutes in the Krebs-Ringer bicarbonate (KRB) buffer with 2 mM glucose (in petri dishes). The KRB medium contains 143.5 mM $Na^+$, 5.8 mM $K^+$, 2.5 mM $Ca^{2+}$, 1.2 mM $Mg^{2+}$, 124.1 mM $Cl^-$, 1.2 mM $PO_4^{3-}$, 1.2 mM $SO_4^{2+}$, 25 mM $CO_3^{2-}$, 2 mg/mL bovine serum albumin (pH 7.4). The islets were then transferred to a 96-well plate (one islet/well) and incubated at 37° C. for 60 minutes in 200 µl of KRB buffer with 2 or 16 mM glucose, and other agents to be tested such as octreotide and a SST3 antagonist. (Zhou et al., *J. Biol. Chem.* 278: 51316-51323, 2003.) Insulin was measured in aliquots of the incubation buffer by ELISA with a commercial kit (ALPCO Diagnostics, Windham, N.H.).

SSTR Binding Assays:

The receptor-ligand binding assays of all 5 subtype of SSTRs were performed with membranes isolated from Chinese hamster ovary (CHO)-K1 cells stably expressing the cloned human somatostatin receptors in 96-well format as previous reported. (Yang et al. *PNAS* 95:10836-10841, 1998, Birzin et al. *Anal. Biochem.* 307:159-166, 2002.) The stable cell lines for SSTR1-SSTR5 were developed by stably transfecting with DNA for all five SSTRs using Lipofectamine. Neomycin-resistant clones were selected and maintained in medium containing 400 µg/mL G418 (Rohrer et al. *Science* 282:737-740, 1998).

SSTR Binding Filtration Assays:

Binding assays were performed using $(3-^{125}I-Tyr11)$-SRIF-14 as the radioligand (used at 0.1 nM) and The Packard Unifilter assay plate. The assay buffer consisted of 50 mM TrisHCl (pH 7.8) with 1 mM EGTA, 5 mM $MgCl_2$, leupeptin (10 µg/mL), pepstatin (10 µg/mL), bacitracin (200 µg/mL), and aprotinin (0.5 µg/mL). CHO-K1 cell membranes, radiolabeled somatostatin, and unlabeled test compounds were resuspended or diluted in this assay buffer. Unlabeled test compounds were examined over a range of concentrations from 0.01 nM to 10,000 nM. The $K_i$ values for compounds were determined as described by Cheng and Prusoff *Biochem Pharmacol.* 22:3099-3108 (1973).

SSTR Binding Scintillation Proximity Assays (SPA):

The receptor-ligand binding Scintillation Proximity Assay (SPA) (N. D. Cook. *Drug Discovery Today* 1 (1996), pp. 287-294) for SSTR3 was performed with membranes isolated from Chinese hamster ovary (CHO)-K1 cells stably expressing the cloned human somatostatin receptors. Binding assays were performed in 384 well format using $^{125}I$-SS14 as the radioligand for SSTR3. The assay buffer consisted of 50 mM TrisHCl (pH 7.8) with 1 mM EGTA, 5 mM $MgCl_2$, leupeptin (10 µg/mL), pepstatin (10 µg/mL), bacitracin (200 µg/mL), and aprotinin (0.5 µg/mL). CHO-K1 cell membranes were prebound to SPA beads and incubated with unlabelled test compounds and radiolabeled somatostatin in assay buffer. After 5 hours at room temperature, cpm/well was determined. Test compounds were examined in 10 point titrations over a range of concentrations from 0.00001 nM to 1200 nM. Percent inhibition was determined for each data point using binding in the presence of DMSO as the maximum achievable value. The results were plotted using 4 parameter fit and the inflection point reflecting 50% of the maximum inhibition was reported as the $IC_{50}$.

The compounds of the present invention, particularly the compounds of Examples 1-22, were tested in the SSTR3 binding assay and found to have $K_i$ and/or $IC_{50}$ values in the range of 600 nM to 0.1 nM against SSTR3, as shown in Table 1, and were found to have $K_i$ and/or $IC_{50}$ values greater than 100 nM against SSTR1, SSTR2, SSTR4, and SSTR5 receptors. Preferred compounds of the present invention were found to have $K_{i/IC_{50}}$ values in the range of 100 nM to 0.1 nM against SSTR3, and $K_{i/IC_{50}}$ values greater than 100 nM against SSTR1, SSTR2, SSTR4, and SSTR5 receptors.

Functional Assay to Assess the Inhibition of SSTR3Mediated Cyclic AMP Production:

The effects of compounds that bind to human and murine SSTR3 with various affinities on the functional activity of the receptor were assessed by measuring cAMP production in the presence of Forskolin (FSK) along or FSK plus SS-14 in SSTR3 expressing CHO cells. FSK acts to induce cAMP production in these cells by activating adenylate cyclases, whereas SS-14 suppresses cAMP production in the SSTR3 stable cells by binding to SSTR3 and the subsequent inhibition of adenylate cyclases via an alpha subunit of GTP-binding protein (Gαi).

To measure the agonism activity of the compounds, we pre-incubated the human or mouse SSTR3 stable CHO cells with the compounds for 15 min, followed by a one-hour incubation of the cells with 3.5 μM FSK (in the continuous presence of the compounds). The amount of cAMP produced during the incubation was quantified with the Lance cAMP assay kit (PerkinElmer, Calif.) according to the manufacturer's instruction. Majority of the compounds described in this application show no or little agonism activity. Therefore we used % Activation to reflect the agonism activity of each compound. The % Activation which was calculated with the following formula:

% Activation=[(*FSK*−Unknown)/(*FSK*−*SS*-14]×100

To measure the antagonism activity of the compounds, we pre-incubated the human or mouse SSTR3 stable CHO cells with the compounds for 15 rain, followed by a one-hour incubation of the cells with a mixture of 3.5 μM FSK+100 nM SS-14 (in the continuous presence of the compounds). The amount of cAMP produced during the incubation was also quantified with the Lance cAMP assay. The antagonism activity of each compound was reflected both by % Inhibition (its maximum ability to block the action of SS-14) and an $EC_{50}$ value which is the concentration of the test compound required to suppress the effect of 100 nM SS-14 by 50%. The % Inhibition of each compound was calculated using the following formula:

% Inhibition=[1−(unknown cAMP/*FSK*+*SS*-14 cAMP)]×100

In some case, 20% of human serum was included in the incubation buffer during the antagonism mode of the function assay to estimate the serum shift of the potency.

The compounds of the present invention, particularly the compounds of Examples 1-22, were tested in the SSTR3 functional antagonist assay and found to have $EC_{50}$ values of less than 2.5 micromolar, as shown in Table 1, and were found to have greater than 80% Inhibition. Preferred compounds of the present invention were found to have $EC_{50}$ values of less than 0.5 micromolar in the SSTR3 antagonist assay, and greater than 80% Inhibition. More preferred compounds of the present invention were found to have $EC_{50}$ values of less than 0.1 micromolar in the SSTR3 antagonist assay, and greater than 85% Inhibition.

Glucose Tolerance Test in Mice:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then challenged with dextrose intraperitoneally-(2-3 g/kg) or orally (3-5 g/kg). One group of vehicle-treated mice is challenged with saline as a negative control. Blood glucose levels are determined from tail bleeds taken at 20, 40, 60 minutes after dextrose challenge. The blood glucose excursion profile from t=0 to t=60 min is used to integrate an area under the curve (AUC) for each treatment. Percent inhibition values for each treatment are generated from the AUC data normalized to the saline-challenged controls. A similar assay may be performed in rats. Compounds of the present invention are active after an oral dose in the range of 0.1 to 100 mg/kg.

Abbreviations used in the Following Schemes and Examples aq.: aqueous; API-ES: atmospheric pressure ionization-electrospray (mass spectrum term); Ac: acetate; AcCN: acetonitrile; Boc: tert-butyloxycarbonyl; Bu is butyl; BuLi: n-butyl lithium; Celite™: diatomaceous earth; CDI: carbonyl diimidazole; D: deuterium; d: day(s); DCM: dichloromethane; DEAD: diethyl azodicarboxylate; DIPEA: N,N-diisopropylethylamine (Hunig's base); DMAP: 4-dimethylaminopyridine; DMF: N,N-dimethylformamide; DMSO: dimethylsulfoxide; EDC: 1-ethyl-3-(3-dimethylaminopropyl)-carbodiimide hydrochloride; EPA: ethylene polyacrylamide (a plastic); eq: equivalent(s); Et is ethyl; EtOAc: ethyl acetate; EtOH: ethanol; g: gram(s); h or hr: hour(s); Hex: hexane; HOBt: 1-hydroxybenzotriazole; HPLC: high pressure liquid chromatography; HPLC/MS: high pressure liquid chromatography/mass spectrum; in vacuo: rotary evaporation under diminished pressure; IBX: 2-iodosobenzoic acid; iPrOH or IPA: isopropyl alcohol; IPAC or IPAc: isopropyl acetate; KHMDS: potassium hexamethyldisilazide; L: liter; LC: Liquid chromatography; LC-MS: liquid chromatography-mass spectrum; LDA: lithium diisopropylamide; M: molar; Me: methyl; MeCN: methylcyanide; MeI: methyl iodide; MeOH: methanol; MHz: megahertz; mg: milligram; min: minute(s); ml or mL: milliliter; mmol: millimole; MPLC: medium-pressure liquid chromatography; MS or ms: mass spectrum; MTBE: methyl tert-butyl ether; N: normal; NaHMDS: sodium hexamethyldisilazide; nm: nanometer; NBS is N-bromosuccinamide; NMR: nuclear magnetic resonance; NMM: N-methylmorpholine; Ph is phenyl; PyBOP: (benzotriazol-1-yloxy)tripyrrolidinophosphonium hexafluorophosphate; $Pd(PPh_3)_2Cl_2$ is bis(triphenylphosphinyl)palladium dichloride; $R_t$: retention time; rt or RT: room temperature; satd.: saturated; SFC: super critical fluid chromatography; TEA: triethylamine; TFA: trifluoroacetic acid; TFAA: trifluoroacetic acid anhydride; THF: tetrahydrofuran; TLC or tlc: thin layer chromatography; Tosyl or Ts: p-toluene sulfonyl; pTSA and TsOH: p-toluene sulfonic acid.

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention. All temperatures are degrees Celsius unless otherwise noted.

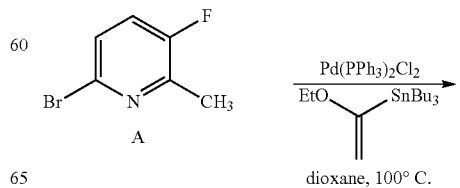

Scheme 1 dioxane, 100° C.

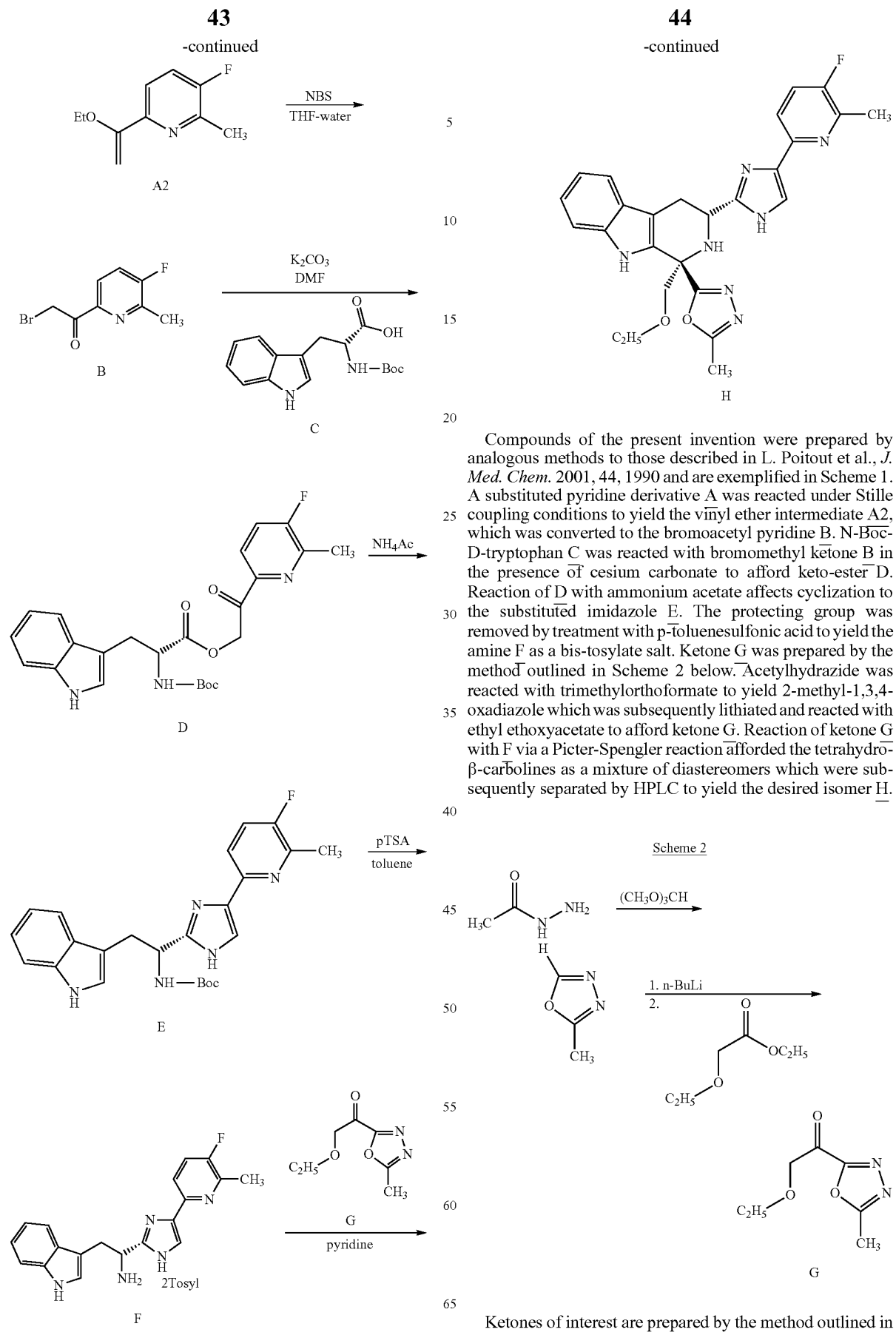

Compounds of the present invention were prepared by analogous methods to those described in L. Poitout et al., *J. Med. Chem.* 2001, 44, 1990 and are exemplified in Scheme 1. A substituted pyridine derivative A was reacted under Stille coupling conditions to yield the vinyl ether intermediate A2, which was converted to the bromoacetyl pyridine B. N-Boc-D-tryptophan C was reacted with bromomethyl ketone B in the presence of cesium carbonate to afford keto-ester D. Reaction of D with ammonium acetate affects cyclization to the substituted imidazole E. The protecting group was removed by treatment with p-toluenesulfonic acid to yield the amine F as a bis-tosylate salt. Ketone G was prepared by the method outlined in Scheme 2 below. Acetylhydrazide was reacted with trimethylorthoformate to yield 2-methyl-1,3,4-oxadiazole which was subsequently lithiated and reacted with ethyl ethoxyacetate to afford ketone G. Reaction of ketone G with F via a Picter-Spengler reaction afforded the tetrahydro-β-carbolines as a mixture of diastereomers which were subsequently separated by HPLC to yield the desired isomer H.

Ketones of interest are prepared by the method outlined in Scheme 2. An acyl hydrazide is reacted with trimethyl orthoformate to afford a 2-substituted 1,3,4-oxadiazole. Lithiation with butyllithium followed by reaction with ethyl ethoxyacetate affords the ethoxymethyl (5-methyl-1,3,4-oxadiazol-2-yl) ketone G.

INTERMEDIATE 1

(1R)-2-(1H-Indol-3-yl)-1-(4-(5-fluoro-pyridin-2-yl)-1H-imidazol-2-yl)-ethylamine ditosylate

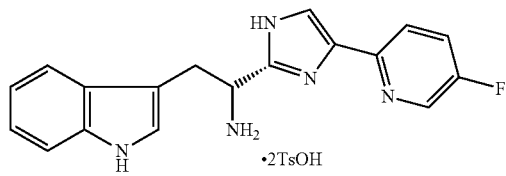

Step A: 2-Chloroacetyl-5-fluoropyridine

2-Bromo-5-fluoropyridine (50.0 g, 284 mmol) in 200 mL of THF was added dropwise over 25 min to isopropylmagnesium chloride (2 M in THF, 284 mL, 568 mmol) at RT, and the mixture was stirred for 2 hours at room temperature. A solution of 2-chloro-N-methoxy-N-methylacetamide (43.0 g, 313 mmol) in 150 mL of THF was added dropwise over 30 minutes to the reaction mixture at RT. The mixture was stirred at RT overnight. The mixture was then poured into 2000 g of ice with 500 mL of 2 N HCl. The mixture was extracted into ether, washed with brine, dried over anhydrous sodium sulfate and concentrated. The resulting residue was dissolved in 1 L of warm hexane and treated with several grams of silica gel to remove colored impurities. The resulting mixture was then filtered, and the filtrate was concentrated and chilled in an ice bath for 30 minutes. The resulting solid was isolated by filtration to give 2-chloroacetyl-5-fluoropyridine. $^1$H NMR (500 MHz, CDCl$_3$): δ 8.53 (d, 1H), 8.19 (dd, 1H), 7.60 (td, 1H), 5.09 (s, 2H).

Step B: tert-Butyl 2-(1H-indol-3-yl)-1-(4-(5-fluoro-pyridin-2-yl)-1H-imidazol-2-yl)-1-ethylcarbamate 2-Chloroacetyl-5-fluoropyridine was converted into tert-butyl 2-(1H-indol-3-yl)-1-(4-(5-fluoro-pyridin-2-yl)-1H-imidazol-2-yl)-1-ethylcarbamate using procedures described in Gordon, T. et al., *Bioorg. Med. Chem. Lett.* 1993, 3, 915; Gordon, T. et al., *Tetrahedron Lett.* 1993, 34, 1901; and Poitout, L. et al., *J. Med. Chem.* 2001, 44, 2990.

A mixture of N-Boc-D-tryptophan (126 g, 415 mmol) and potassium carbonate (31.5 g, 228 mmol) in DMF (700 ml) was stirred at RT 10 min. Then 2-Chloroacetyl-5-fluoropyridine (72 g, 415 mmol) was added portionwise, as a solid, over 3 min. The mixture was stirred overnight. Then the reaction was poured into water (3 L) and extracted with 2×2 L of EtOAc. The extracts were combined, washed two times with water, and then with saturated brine. The organic layer was dried over Na$_2$SO$_4$, filtered through a pad of silica gel, and concentrated to give a light brown solid, which was titurated in ~1 L of ether, and then chilled in an ice bath. The resulting solid was filtered, washed with ether, and air dried to give the ester intermediate as a cream colored solid, which was used in the subsequent reaction.

The ester intermediate (133 g) was mixed with ammonium acetate (186 g) in p-xylene (2 L). The reaction mixture was heated to reflux for 2 hr with a Dean-Stark trap attached. Then the mixture was cooled to RT and diluted with 2 L of EtOAc. The layers were separated, and the aqueous layer was extracted with an additional 1.5 L of EtOAc. The organic layers were combined, washed with water (2×1 L), saturated NaHCO$_3$, and brine, and then dried over Na$_2$SO$_4$, and concentrated to ~1 L. After standing for 2 hr, the resulting product was filtered, washed with ether and air dried to afford tert-Butyl 2-(1H-indol-3-yl)-1-(4-(5-fluoro-pyridin-2-yl)-1H-imidazol-2-yl)-1-ethylcarbamate as a cream colored powder. LC-MS: m/e 422.4 (M+H)$^+$ (2.49 min). $^1$H NMR (500 MHz, DMSO-d6): δ 12.03 (s, 1H), 10.75 (s, 1H), 8.46 (s, 1H), 7.90 (m, 1H), 7.67 (t, 1H), 7.55 (m, 2H), 7.30 (d, 1H), 7.14 (d, 1H), 7.08-6.92 (m, 4H), 4.91 (m, 1H), 3.34 (m, 1H), 3.17 (m, 1H), 1.33 (s, 9H).

Step C: 2-(1H-Indol-3-yl)-1-(4-(5-fluoro-pyridin-2-yl)-1H-imidazol-2-yl)-ethylamine tert-Butyl 2-(1-indol-3-yl)-1-(4-(5-fluoro-pyridin-2-yl)-1H-imidazol-2-yl)-1-ethylcarbamate (100 g, 237 mmol) was added to CH$_3$CN and stirred for 5 min. Additional CH$_3$CN was added gradually until the total volume was 1.6 L, followed by the addition of p-toluenesulfonic acid monohydrate (149 g, 783 mmol). The mixture was heated to 60° C. for 1 hr, and then cooled to RT. The resulting solid was separated by filtration, washed with CH$_3$CN, and air-dried to give 2-(1H-indol-3-yl)-1-(4-(5-fluoro-pyridin-2-yl)-1H-imidazol-2-yl)-ethylamine. LC-MS: m/e 322.4 (M+H)$^+$ (1.92 min). $^1$H NMR (500 MHz, CD$_3$OD): δ 8.54 (s, 1H), 8.05-7.97 (m, 2H), 7.89 (td, 1H), 7.69 (d, 4H), 7.43 (d, 1H), 7.31 (d, 1H), 7.18 (d, 4H), 7.10-7.03 (m, 2H), 6.95 (t, 1H), 5.03 (dd, 1H), 3.70-3.59 (m, 2H), 2.32 (s, 6H).

INTERMEDIATE 2

(1R)-2-(1H-Indol-3-yl)-1-(4-(5-fluoro-6-methyl-pyridin-2-yl)-1H-imidazol-2-yl)-ethylamine ditosylate

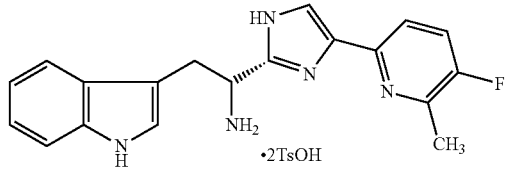

Step A:
2-(1-Ethoxy-ethenyl)-5-fluoro-6-methyl-pyridine

A mixture of 2-bromo-5-fluoro-6-methylpyridine (25 g, 132 mmol), 1-ethoxyvinyltri-n-butyltin (48.9 ml, 145 mmol) and bis(triphenylphosphine)palladium (II) chloride (4.62 g, 6.58 mmol) in 1,4-dioxane (250 ml) was heated to 100° C. under nitrogen over night. The reaction was then cooled to room temperature and the solvent was removed in vacuo. The residue was purified by silica gel chromatography (eluted with a gradient of ethyl acetate in hexanes) to give the product 2-(1-ethoxy-ethenyl)-5-fluoro-6-methyl-pyridine, together with an unidentified impurity. This product was used in the next step. $^1$H NMR (500 MHz, CDCl$_3$): δ 7.51 (dd, 1H), 7.28 (t, 1H), 5.33 (d, 1H), 4.31 (d, 1H), 3.96 (q, 2H), 2.53 (d, 3H), 1.43 (t, 3H).

Step B: 2-Bromoacetyl-5-fluoro-6-methyl-pyridine

A solution of 2-(1-ethoxy-ethenyl)-5-fluoro-6-methyl-pyridine obtained from Step A (15.3 g) in THF (200 mL) and water (8 mL) was treated with N-bromosuccinimide (12.02 g) at room temperature. After stirring for 10 min, the reaction was concentrated in vacuo. The resulting residue was purified by silica gel chromatography (eluted with a gradient of ethyl acetate in hexanes) to give 2-bromoacetyl-5-fluoro-6-methyl-pyridine, together with an unidentified impurity. This product was used in the next step. $^1$H NMR (500 MHz, CDCl$_3$): δ 7.98 (dd, 1H), 7.44 (t, 1H), 4.83 (s, 2H), 2.57 (d, 3H).

Step C: (1R)-2-(1H-Indol-3-yl)-1-(4-(5-fluoro-6-methyl-pyridin-2-yl)-1H-imidazol-2-yl)-ethylamine bis-tosylate salt 2-Bromoacetyl-5-fluoro-6-methyl-pyridine was reacted with N-t-butyloxycarbonyl-D-tryptophan according to the procedures described for the preparation of Intermediate 1, Steps B and C to afford (1R)-2-(1H-Indol-3-yl)-1-(4-(5-fluoro-6-methyl-pyridin-2-yl)-1H-imidazol-2-yl)-ethylamine bis-tosylate salt.

N-Boc-D-tryptophan (7.8 g, 25.6 mmol) was dissolved in DMF (40 ml) and treated with K$_2$CO$_3$ (1.948 g, 14.10 mmol). The mixture was stirred for 10 min, followed by the addition of 2-bromoacetyl-5-fluoro-6-methyl-pyridine (7.24 g, 24.35 mmol) in 20 mL of DMF. The mixture was stirred for 2 h at RT. The reaction was filtered to discard the solid. The filtrate was treated with water, and the resulting mixture was extracted with ethyl acetate. The organic layer was washed with water and brine, and dried (Na$_2$SO$_4$) to give a residue. The residue was purified by MPLC by eluting with 5% to 50% ethyl acetate in hexanes to afford the ester intermediate. LC-MS: m/e 456.24 (M+H)$^+$ (3.38 min, 7 min method).

The ester intermediate (10 g) was treated with ammonium acetate (39.5 g, 513 mmol) and p-xylene (200 ml) and heated in oil bath (160° C.) for 4 h. Then the reaction mixture was cooled to RT. Aqueous extraction with ethyl acetate, followed by washing with water and brine, and then drying (Na$_2$SO$_4$) and concentrating afforded the imidazole intermediate. The imidazole intermediate was converted to (1R)-2-(1H-Indol-3-yl)-1-(4-(5-fluoro-6-methyl-pyridin-2-yl)-1H-imidazol-2-yl)-ethylamine bis-tosylate salt, using the procedure described above for Intermediate 1, Step C. $^1$H NMR (500 MHz, CD$_3$OD): δ 8.02 (s, 1H), 7.86 (dd, 1H), 7.81 (m, 1H), 7.68 (d, 4H), 7.44 (d, 1H), 7.32 (d, 1H), 7.18 (d, 4H), 7.08 (m, 2H), 6.96 (t, 1H), 5.02 (t, 1H), 3.64 (m, 2H), 2.58 (s, 3H), 2.32 (s, 6H); LC-MS: m/e 336.12 (M+H)$^+$ (1.35 min, 4 min method).

INTERMEDIATE 3

Ethoxymethyl 5-methyl-1,3,4-oxadiazol-4-yl ketone

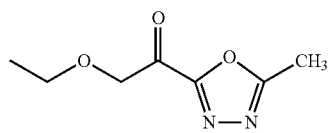

Step A: 2-Methyl-1,3,4-Oxadiazole

To a mixture of acetic hydrazide (53.0 g, 715 mmol) in trimethyl orthoformate (395 mL, 3577 mmol) was added p-toluenesulfonic acid monohydrate (13.61 g, 71.5 mmol). The mixture was heated in a 125° C. bath. After heating the reaction overnight (16 hours), the reaction was allowed to cool and concentrated to about 200 mL. The resulting residue was purified on a flash chromatography column (Biotage™-65) using a gradient of 0-100% of n-hexane/Et$_2$O to give the desired product. $^1$H NMR (500 MHz, CD$_3$OD): δ 2.57 (s, 3H), 8.84 (s, 1H).

Step B: Ethoxymethyl 5-methyl-1,3,4-oxadiazol-2-yl ketone

To a stirred solution of the 2-methyl-1,3,4-oxadiazole (5.0 g, 59.5 mmol) in THF (100 mL) was added dropwise n-BuLi (23.79 mL, 59.5 mmol) in toluene under N$_2$ at −78° C. After 1 h, ethyl ethoxyacetate (10.22 g, 77 mmol) was added. The reaction mixture was then allowed to warm to −40° C. and stirred for 2 h. The reaction mixture was then quenched with 65 mL of LON HCl and extracted with EtOAc. The organic layer was washed with water and then brine, dried over anhydrous Na$_2$SO$_4$, and concentrated. The resulting residue was purified on a flash chromatography column (Biotage™-40M) using a gradient of 0-100% of n-hexane/Et$_2$O to give the desired product. $^1$H NMR (500 MHz, CD$_3$OD): δ 1.27 (t, 3H), 2.64 (s, 3H), 3.69 (q, 2H), 4.88 (s, 2H).

EXAMPLES 1 AND 2

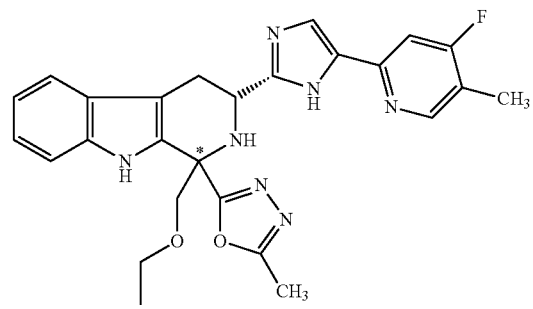

To a solution of ethoxymethyl 5-methyl-1,3,4-oxadiazol-2-yl ketone (Intermediate 3, 5.0 g, 29.4 mmol) in pyridine (50 mL) were added (1R)-2-(1H-Indol-3-yl)-1-(4-(5-fluoro-6-methyl-pyridin-2-yl)-1H-imidazol-2-yl)-ethylamine ditosylate (Intermediate 2, 20.0 g, 29.4 mmol) and tetraethoxysilane (13.18 mL, 58.8 mmol). The mixture was heated in a 80° C. bath. After heating the reaction overnight (12 hours), the reaction was allowed to cool and diluted with EtOAc. The organic layer was washed with water (3 times) and then brine, dried over anhydrous Na$_2$SO$_4$, and concentrated. The resulting residue was purified on two flash chromatography columns (Biotage™-65) using a gradient of 0-100% of solvent B in Hexane where solvent B is 48:50:2 Et$_2$O/EtOAc/NH$_4$OH, but the mixture of isomers at the * position did not separate. The mixture of isomers at the * position was then separated by SFC on a Chiralpak™ AS column using 20% (i-propanol+0.2% DEA) to give the faster isomer (Isomer A) and the slow isomer (Isomer B). On an analytical SFC Chiralpak™ AS column eluting with 20% (MeOH+0.2% DEA), the faster isomer had a Rt=3.44 minutes, and the slower isomer had a Rt=4.25 minutes.

Isomer A, Example 1: LCMS m/e=488.19, 2.53 min; $^1$H NMR (500 MHz, CD$_3$OD): δ 1.16 (t, 3H), 2.53 (s, 6H), 3.09

(m, 1H), 3.22 (m, 1H), 3.60 (q, 2H), 4.18 (1H, dd, J=9.7 Hz), 4.23 (1H, dd, J=9.8 Hz), 4.72 (m, 1H), 7.03-7.74 (m, 7H).

Isomer B, Example 2: LCMS m/e=488.22, 2.54 min; $^1$H NMR (500 MHz, CD$_3$OD): δ 1.17 (t, 3H), 2.53 (s, 3H), 2.55 (s, 3H), 3.13 (m, 1H), 3.20 (m, 1H), 3.59 (m, 2H), 4.11 (1H, dd, J=9.3 Hz), 4.17 (1H, dd, J=9.2 Hz), 4.52 (m, 1H), 7.03-7.76 (m, 7H).

The compounds listed in the Examples in Table 1 were prepared according to the procedure for Examples 1 and 2 by reacting either Intermediate 1 or Intermediate 2 with the appropriate ketone. For Examples 3-22, a pair of diastereomers was obtained and separated according to the procedures in Example 1 and 2. Only data for the more active isomer is reported in Table 1.

TABLE 1

| Example No | Structure | LC-MS | Retention Time (min) | Human SSTR3 Filtration Assay Ki (nm) | Human SSTR3 SPA Assay IC$_{50}$ (nM) | Human SSTR3 Antagonist EC$_{50}$ (nM) | MK-499 binding IC$_{50}$ (μM) |
|---|---|---|---|---|---|---|---|
| 3 | 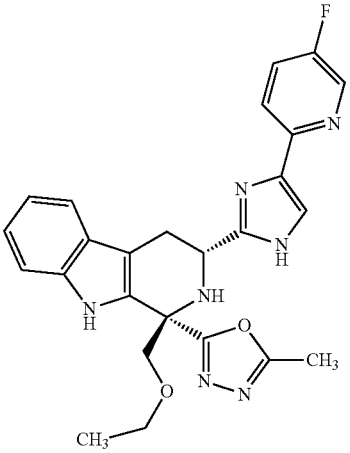 [SMILES: CCOC[C@]1(c2nnc(C)o2)N[C@@H](c2nc(-c3ccc(F)cn3)c[nH]2)Cc2c1[nH]c1ccccc21] | 488.19 | 2.53 | 6.4 | 43.8 | 45.8 | 18.1 |
| 4 | 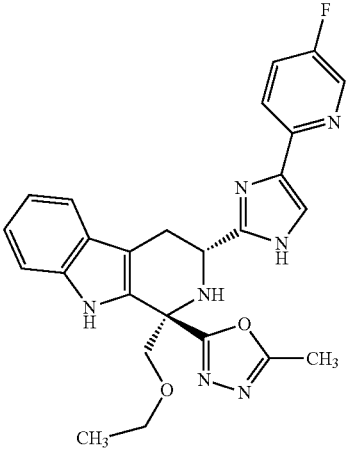 [SMILES: CCOC[C@@]1(c2nnc(C)o2)N[C@@H](c2nc(-c3ccc(F)cn3)c[nH]2)Cc2c1[nH]c1ccccc21] | 488.22 | 2.54 | 0.7 | 2.6 | 2.2 | 20.1 |

TABLE 1-continued
| Example No | Structure | LC-MS | Retention Time (min) | Human SSTR3 Filtration Assay Ki (nm) | Human SSTR3 SPA Assay IC$_{50}$ (nM) | Human SSTR3 Antagonist EC$_{50}$ (nM) | MK-499 binding IC$_{50}$ (μM) |
|---|---|---|---|---|---|---|---|
| 5 | 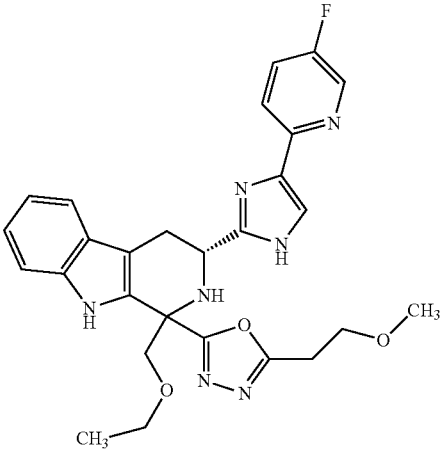 [SMILES: CCOCC1(c2nnc(CCOC)o2)N[C@@H](c2nc(-c3ccc(F)cn3)c[nH]2)Cc2c1[nH]c1ccccc21] | 518.16 | 2.64 | 2.7 | nd | 3.5 | 16.5 |
| 6 | 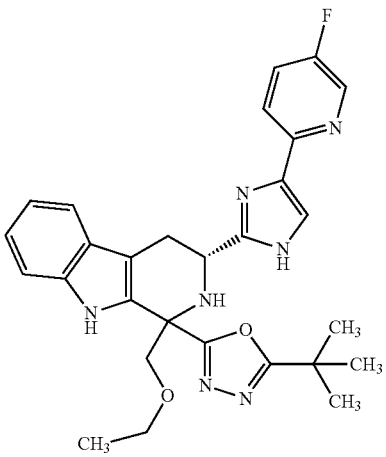 [SMILES: CCOCC1(c2nnc(C(C)(C)C)o2)N[C@@H](c2nc(-c3ccc(F)cn3)c[nH]2)Cc2c1[nH]c1ccccc21] | 516.24 | 2.87 | 2.6 | nd | 2.5 | 17.9 |
| 7 | 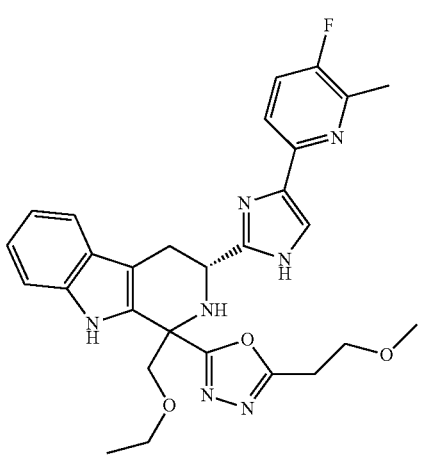 [SMILES: CCOCC1(c2nnc(CCOC)o2)N[C@@H](c2nc(-c3ccc(F)c(C)n3)c[nH]2)Cc2c1[nH]c1ccccc21] | 532.29 | 2.85 | 0.9 | nd | 0.9 | 23.2 |

TABLE 1-continued

| Example No | Structure | LC-MS | Retention Time (min) | Human SSTR3 Filtration Assay Ki (nm) | Human SSTR3 SPA Assay IC$_{50}$ (nM) | Human SSTR3 Antagonist EC$_{50}$ (nM) | MK-499 binding IC$_{50}$ (μM) |
|---|---|---|---|---|---|---|---|
| 8 | 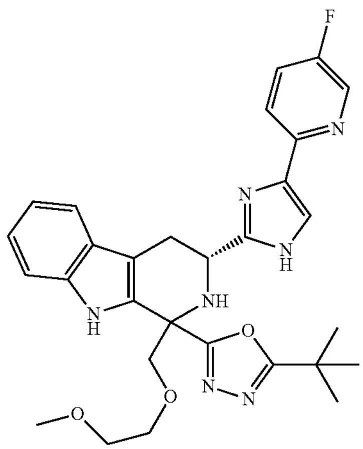 [SMILES: COCCOCC1(c2nnc(C(C)(C)C)o2)N[C@@H](c2nc(-c3ccc(F)cn3)c[nH]2)Cc2c1[nH]c1ccccc21] | 546.28 | 2.88 | 1.4 | nd | 3.7 | 19.7 |
| 9 | 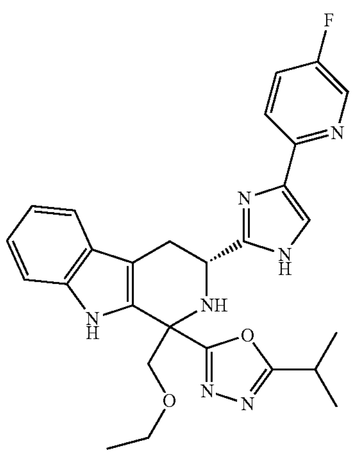 [SMILES: CCOCC1(c2nnc(C(C)C)o2)N[C@@H](c2nc(-c3ccc(F)cn3)c[nH]2)Cc2c1[nH]c1ccccc21] | 502.27 | 2.85 | 2.5 | nd | 5.1 | 20.2 |
| 10 | 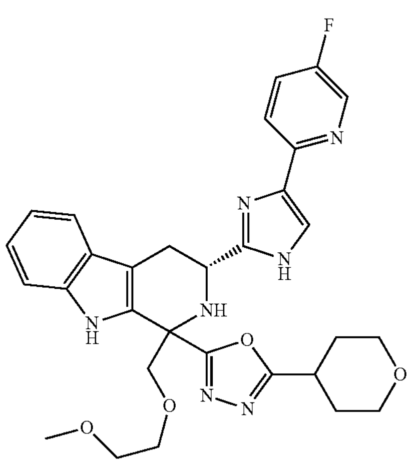 [SMILES: COCCOCC1(c2nnc(C3CCOCC3)o2)N[C@@H](c2nc(-c3ccc(F)cn3)c[nH]2)Cc2c1[nH]c1ccccc21] | 574.33 | 2.60 | 2.7 | nd | 2.4 | 23.4 |

TABLE 1-continued
| Example No | Structure | LC-MS | Retention Time (min) | Human SSTR3 Filtration Assay Ki (nm) | Human SSTR3 SPA Assay IC$_{50}$ (nM) | Human SSTR3 Antagonist EC$_{50}$ (nM) | MK-499 binding IC$_{50}$ (μM) |
|---|---|---|---|---|---|---|---|
| 11 | 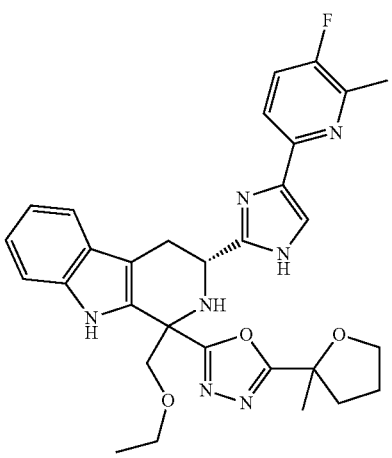 [SMILES: CCOCC1(c2nnc(C3(C)CCCO3)o2)N[C@@H](c2nc(-c3ccc(F)c(C)n3)c[nH]2)Cc2c1[nH]c1ccccc21] | 558.43 | 2.83 | 0.5 | nd | 0.7 | 19.2 |
| 12 | 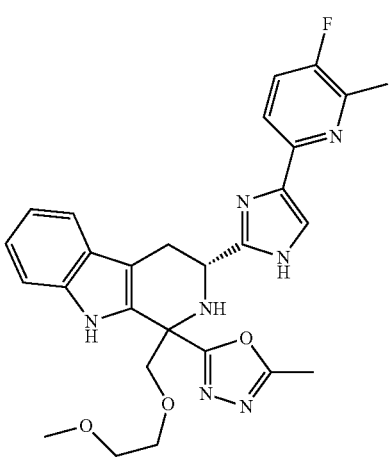 [SMILES: COCCOCC1(c2nnc(C)o2)N[C@@H](c2nc(-c3ccc(F)c(C)n3)c[nH]2)Cc2c1[nH]c1ccccc21] | 518.31 | 2.68 | 0.4 | nd | 1.0 | 27.7 |
| 13 | 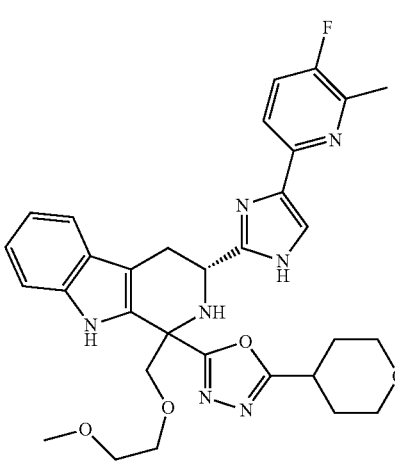 | 588.32 | 2.78 | 0.5 | nd | 0.5 | 19.6 |

TABLE 1-continued

| Example No | Structure | LC-MS | Retention Time (min) | Human SSTR3 Filtration Assay Ki (nm) | Human SSTR3 SPA Assay IC$_{50}$ (nM) | Human SSTR3 Antagonist EC$_{50}$ (nM) | MK-499 binding IC$_{50}$ (μM) |
|---|---|---|---|---|---|---|---|
| 14 | 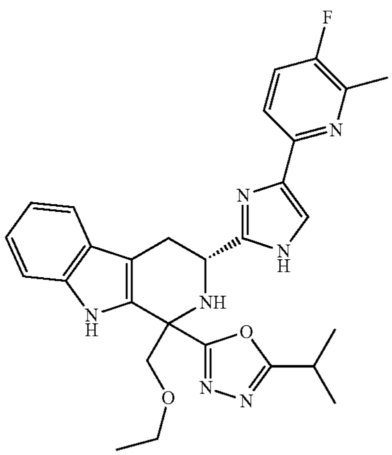 [SMILES: CCOCC1(c2nnc(C(C)C)o2)N[C@@H](c2nc(-c3ccc(F)c(C)n3)c[nH]2)Cc2c1[nH]c1ccccc21] | 516.33 | 2.98 | 0.4 | nd | 1.3 | 18.6 |
| 15 | 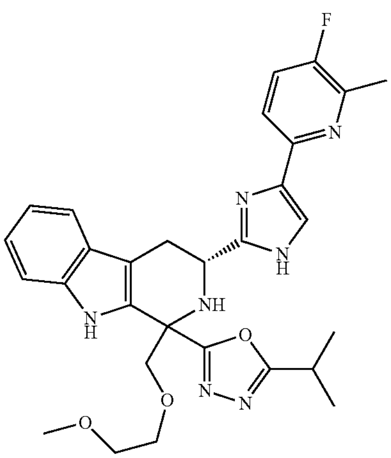 [SMILES: COCCOCC1(c2nnc(C(C)C)o2)N[C@@H](c2nc(-c3ccc(F)c(C)n3)c[nH]2)Cc2c1[nH]c1ccccc21] | 546.35 | 2.96 | 0.4 | nd | 0.6 | 19.2 |
| 16 | 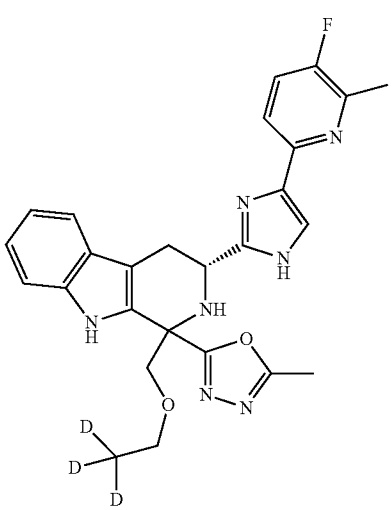 [SMILES: [2H]C([2H])([2H])COCC1(c2nnc(C)o2)N[C@@H](c2nc(-c3ccc(F)c(C)n3)c[nH]2)Cc2c1[nH]c1ccccc21] | 491.27 | 2.53 | 0.6 | nd | 8.5 | 22.3 |

TABLE 1-continued
| Example No | Structure | LC-MS | Retention Time (min) | Human SSTR3 Filtration Assay Ki (nm) | Human SSTR3 SPA Assay IC$_{50}$ (nM) | Human SSTR3 Antagonist EC$_{50}$ (nM) | MK-499 binding IC$_{50}$ (μM) |
|---|---|---|---|---|---|---|---|
| 17 | 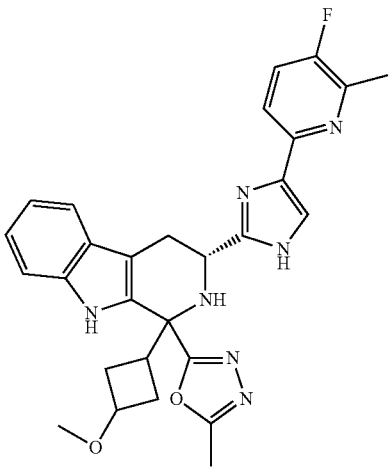 [SMILES: COC1CC(C2(c3nnc(C)o3)N[C@@H](c3nc(-c4ccc(F)c(C)n4)c[nH]3)Cc3c2[nH]c2ccccc32)C1] | 514.29 | 2.59 | 1.8 | nd | 1.7 | 21.6 |
| 18 | 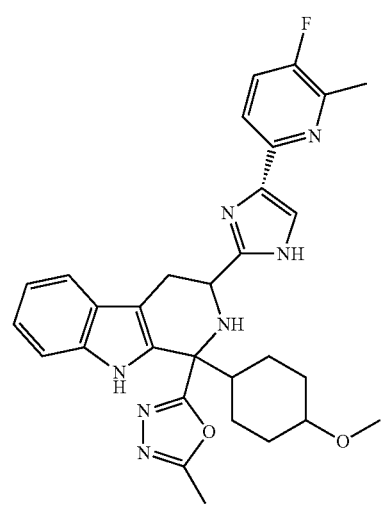 | 541.62 | 2.74 | 0.3 | nd | 0.6 | 17.5 |
| 19 | 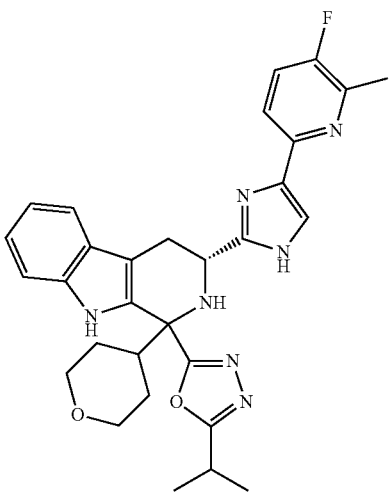 [SMILES: Cc1nc(-c2c[nH]c([C@H]3Cc4c([nH]c5ccccc45)C(c4nnc(C(C)C)o4)(C4CCOCC4)N3)n2)ccc1F] | 542.33 | 2.68 | 0.6 | nd | 0.7 | 16.0 |

TABLE 1-continued

| Example No | Structure | LC-MS | Retention Time (min) | Human SSTR3 Filtration Assay Ki (nm) | Human SSTR3 SPA Assay IC$_{50}$ (nM) | Human SSTR3 Antagonist EC$_{50}$ (nM) | MK-499 binding IC$_{50}$ (μM) |
|---|---|---|---|---|---|---|---|
| 20 | 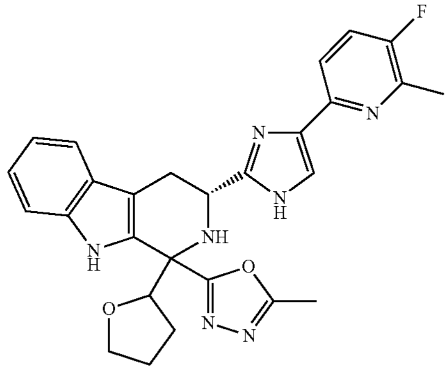 [SMILES: Cc1nnc(C2(C3CCCO3)N[C@@H](c3nc(-c4ccc(F)c(C)n4)c[nH]3)Cc3c2[nH]c2ccccc32)o1] | 500.05 | 1.14 | 0.9 | 4.6 | 4.0 | 17.0 |
| 21 | 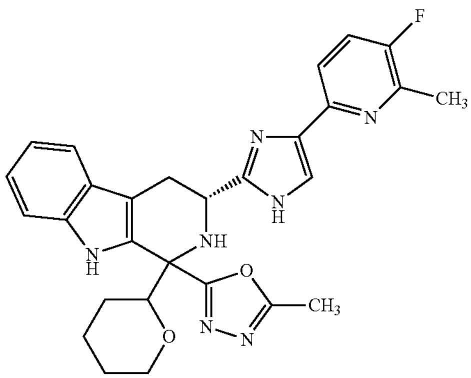 [SMILES: Cc1nnc(C2(C3CCCCO3)N[C@@H](c3nc(-c4ccc(F)c(C)n4)c[nH]3)Cc3c2[nH]c2ccccc32)o1] | 514.07 | 1.13 | nd | 1.7 | 3.1 | 14.6 |
| 22 | 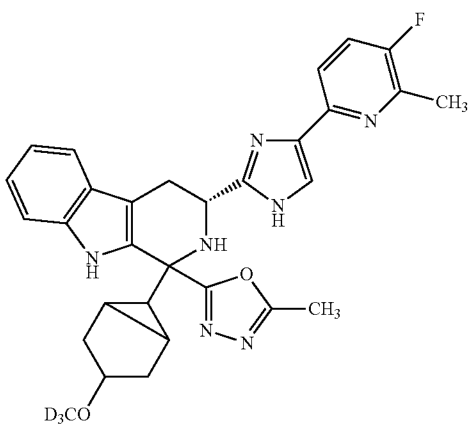 | 543.16 | 2.67 | nd | 1.2 | 1.57 | 22.8 |

The term "nd" means not determined.
OD column refers to Chiralcel ™ OD column using an isopropanol/heptane solvent system.
AD column refers to ChiralPak ™ AD column using an isopropanol/heptane solvent system.

EXAMPLE OF A PHARMACEUTICAL FORMULATION

As a specific embodiment of an oral composition of a compound of the present invention, 50 mg of the compound of any of the Examples is formulated with sufficient finely divided lactose to provide a total amount of 580 to 590 mg to fill a size 0 hard gelatin capsule.

As a second specific embodiment of an oral composition of a compound of the present invention, 100 mg of the compound of any of the Examples, microcrystalline cellulose (124 mg), croscarmellose sodium (8 mg), and anhydrous unmilled dibasic calcium phosphate (124 mg) are thoroughly mixed in a blender; magnesium stearate (4 mg) and sodium stearyl fumarate (12 mg) are then added to the blender, mixed, and the mix transferred to a rotary tablet press for direct compression. The resulting tablets are unsubstituted or film-coated with Opadry® II for taste masking.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula I:

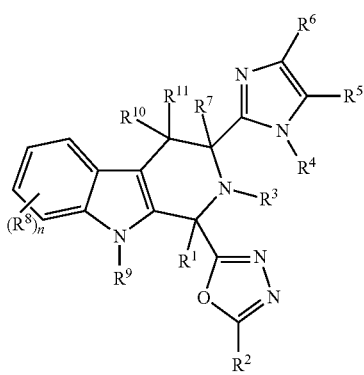

and pharmaceutically acceptable salts thereof, wherein:
$R^1$ is selected from the group consisting of:
(1) —$C_{1-6}$ alkyl-O—$C_{1-6}$ alkyl,
(2) —$C_{1-6}$ alkyl-O—$C_{1-6}$ alkyl-O—$C_{1-6}$ alkyl,
(3) —$C_{3-10}$ cycloalkyl, and
(4) —$C_{3-10}$ cycloheteroalkyl,
wherein alkyl, cycloalkyl and cycloheteroalkyl are unsubstituted or substituted with one to three substituents independently selected from $R^a$;
each $R^2$ is independently selected from the group consisting of:
(1) —$C_{1-6}$alkyl,
(2) —$C_{1-6}$ alkyl-O—$C_{1-6}$ alkyl, and
(3) —$C_{3-6}$ cycloheteroalkyl,
wherein alkyl and cycloheteroalkyl are unsubstituted or substituted with one to three substituents independently selected from $R^f$;
$R^3$, $R^4$, $R^5$, $R^7$, $R^8$, $R^9$, $R^{10}$, and $R^{11}$ are each hydrogen;
$R^6$ is pyridine, wherein pyridine is substituted with two substituents independently selected from $R^i$;
each $R^a$ is independently selected from the group consisting of:
(1) —$C_{1-6}$ alkyl,
(2) —$OC_{1-6}$ alkyl,
(5) halogen,
(18) —$CF_3$,
(19) —$OCF_3$, and
(20) —$OCHF_2$;
$R^f$ is selected from the group consisting of:
(1) halogen, and
(2) —$C_{1-10}$ alkyl, unsubstituted or substituted with one to five fluorines;

each $R^i$ is independently selected from the group consisting of:
(3) halogen,
(16) —$CF_3$,
(17) —$OCF_3$,
(18) —$OCHF_2$, and
(19) —$C_{1-10}$ alkyl; and
n is 0, 1, 2, 3 or 4;
or a pharmaceutically acceptable salt thereof.

2. The compound of claim 1 wherein $R^a$ is —$OC_{1-6}$ alkyl; $R^f$ is —$C_{1-6}$ alkyl; and each $R^i$ is independently selected from the group consisting of: halogen and —$C_{1-6}$alkyl; or a pharmaceutically acceptable salt thereof.

3. The compound of claim 1 wherein $R^6$ is pyridin-2-yl, wherein pyridine is substituted with two substituents independently selected from $R^i$; or a pharmaceutically acceptable salt thereof.

4. The compound of claim 3 wherein $R^6$ is pyridin-2-yl, wherein pyridine is substituted with two substituents independently selected from halogen and $C_{1-6}$alkyl; or a pharmaceutically acceptable salt thereof.

5. The compound of claim 4 wherein $R^6$ is 5-fluoro-6-methyl-pyridin-2-yl; or a pharmaceutically acceptable salt thereof.

6. The compound of claim 1 wherein $R^1$ is selected from the group consisting of:
(1) —$C_{1-6}$ alkyl-O—$C_{1-6}$ alkyl,
(2) —$C_{1-6}$ alkyl-O—$C_{1-6}$ alkyl-O—$C_{1-6}$ alkyl,
(3) —$C_{3-10}$ cycloalkyl, and
(4) —$C_{3-10}$ cycloheteroalkyl,
wherein alkyl, cycloalkyl and cycloheteroalkyl are unsubstituted or substituted with one to two substituents independently selected from —O—$C_{1-6}$ alkyl; or a pharmaceutically acceptable salt thereof.

7. The compound of claim 1 wherein $R^1$ is selected from the group consisting of:
(1) —$CH_2$—O—$CH_2CH_3$,
(2) —$CH_2$—O—$CH_2CD_3$,
(3) —$CH_2$—O—$CH_2CH_2$—O—$CH_3$,
(4) cyclobutyl,
(5) cyclohexyl,
(6) bicyclo[3.1.0]hexane,
(7) tetrahydropyran, and
(8) tetrahydrofuran,
wherein alkyl, cyclobutyl, cyclohexyl, bicyclo[3.1.0]hexane, tetrahydropyran, and tetrahydrofuran are unsubstituted or substituted with one to three substituents independently selected from $R^a$; or a pharmaceutically acceptable salt thereof.

8. The compound of claim 6 wherein $R^1$ is —$C_{1-6}$ alkyl-O—$C_{1-6}$ alkyl, wherein alkyl is unsubstituted or substituted with one to three substituents independently selected from $R^a$; or a pharmaceutically acceptable salt thereof.

9. The compound of claim 1 wherein $R^2$ is —$C_{1-6}$ alkyl, wherein alkyl is unsubstituted or substituted with one to three substituents independently selected from $R^f$; or a pharmaceutically acceptable salt thereof.

10. The compound of claim 1 wherein:
$R^1$ is selected from the group consisting of:
(1) —$CH_2$—O—$CH_2CH_3$,
(2) —$CH_2$—O—$CH_2$Chd3,
(3) —$CH_2$—O—$CH_2CH_2$—O—$CH_3$,
(4) cyclobutyl,
(5) cyclohexyl,
(6) bicyclo[3.1.0]hexane, (7) tetrahydropyran, and (8) tetrahydrofuran, wherein alkyl, cyclobutyl, cyclohexyl, bicyclo[3.1.0]hexane, tetrahydropyran, and tetrahydrofuran are unsubstituted or substituted with one to three substituents independently selected from $R^a$;

$R^3$, $R^4$, $R^5$, $R^7$, $R^8$, $R^9$, $R^{10}$, and $R^{11}$ are each hydrogen;

$R^6$ is pyridin-2-yl, wherein pyridine is substituted with two substituents independently selected from $R^1$; and $R^2$ is selected from the group consisting of:

(1) —CH$_3$, (2) —C(CH$_3$)$_3$, (3) —CH(CH$_3$)$_2$, (4) —CH$_2$CH$_2$—O—CH$_3$, (5) tetrahydropyran, and (6) tetrahydrofuran, wherein alkyl, tetrahydropyran, and tetrahydrofuran are unsubstituted or substituted with one to three substituents independently selected from $R^f$;

or a pharmaceutically acceptable salt thereof.

11. The compound of claim 10 wherein:

$R^1$ is —C$_{1-6}$ alkyl-O—C$_{1-6}$ alkyl, wherein alkyl is unsubstituted or substituted with one to three substituents independently selected from $R^a$;

$R^6$ is pyridin-2-yl, wherein pyridine is substituted with two substituents independently selected from halogen and C$_{1-6}$alkyl;

$R^2$ is —C$_{1-6}$ alkyl, wherein alkyl is unsubstituted or substituted with one to three substituents independently selected from $R^f$;

or a pharmaceutically acceptable salt thereof.

12. The compound of claim 1 of structural formula II having the indicated R stereochemical configuration at the stereogenic carbon atom marked with an *:

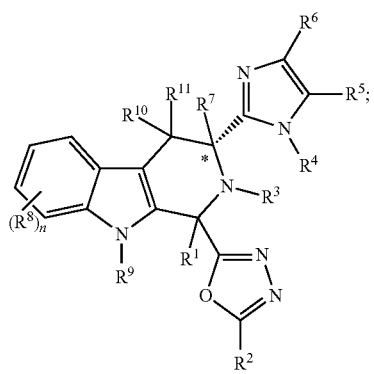

or a pharmaceutically acceptable salt thereof.

13. The compound of claim 1 selected from the group consisting of:

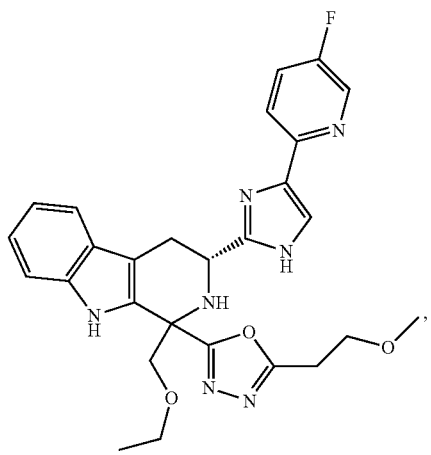

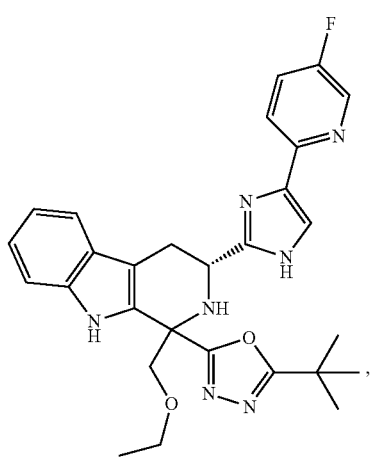

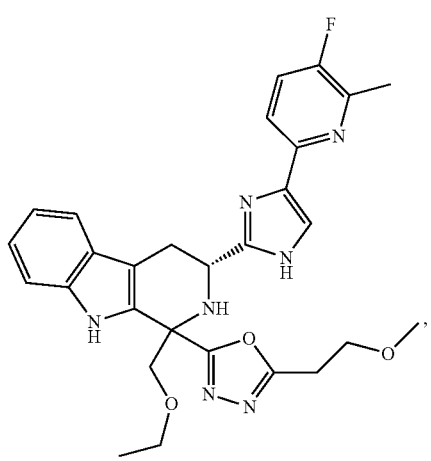

67
-continued
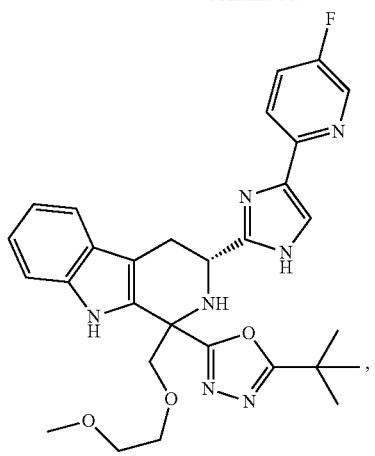
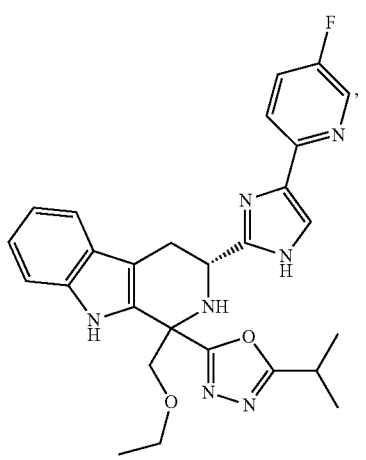
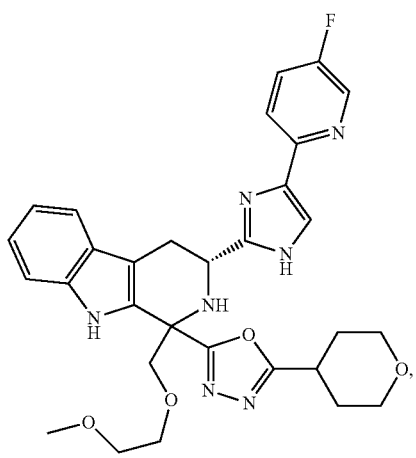
68
-continued
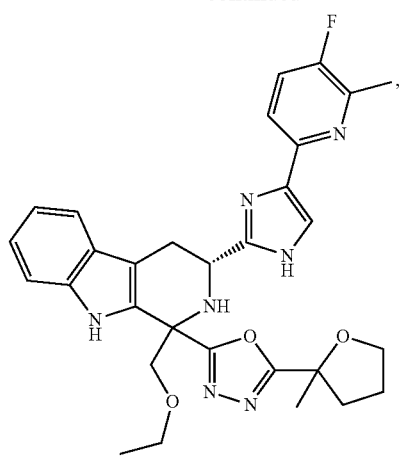
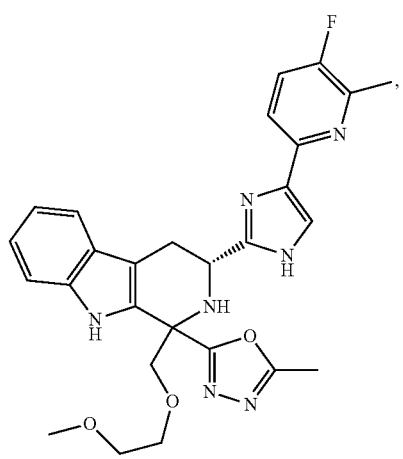
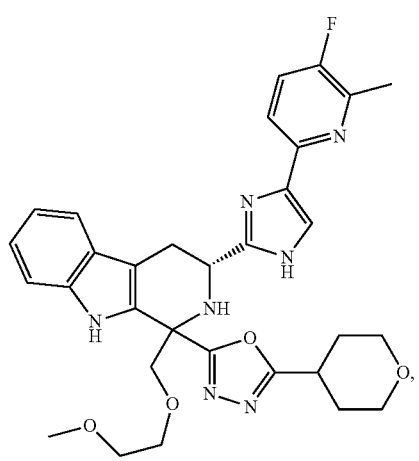

69
-continued
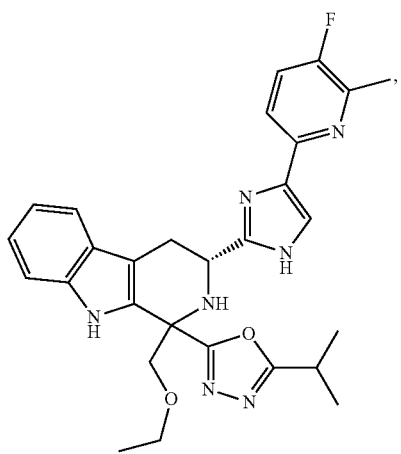
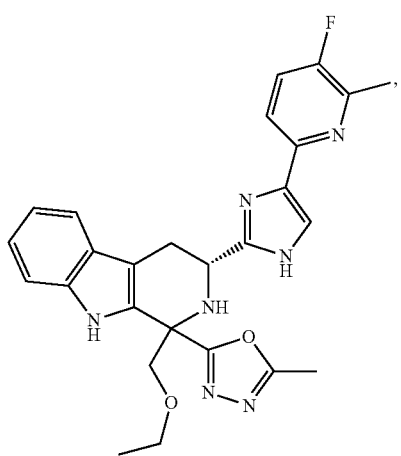
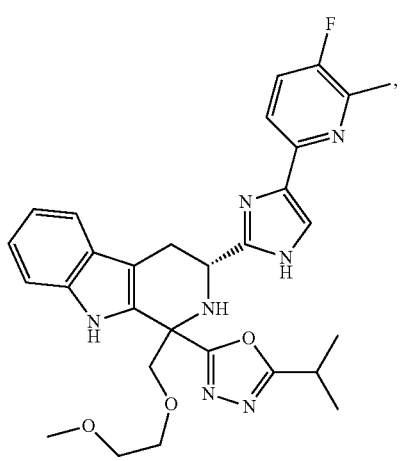
70
-continued
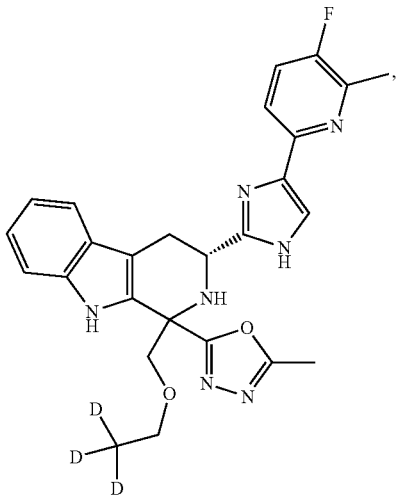
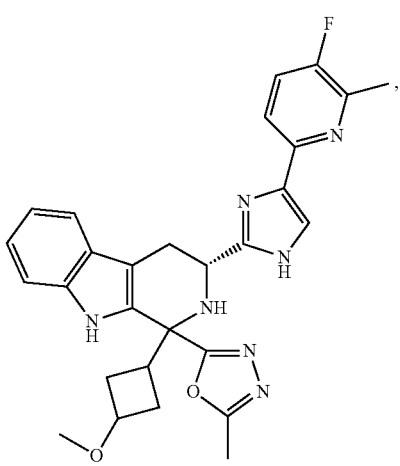
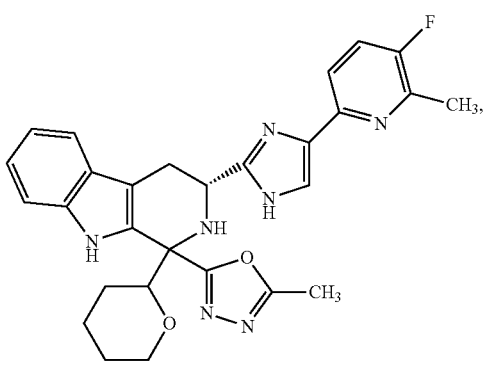

71
-continued
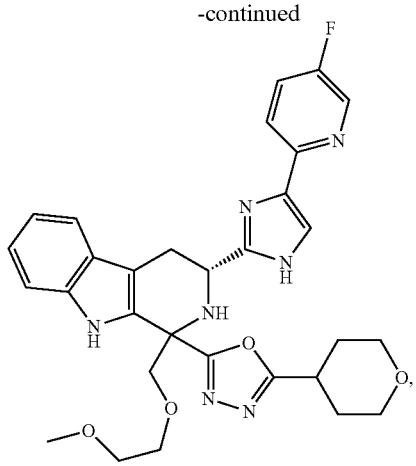
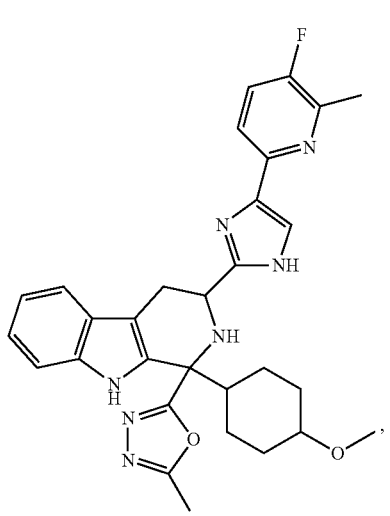
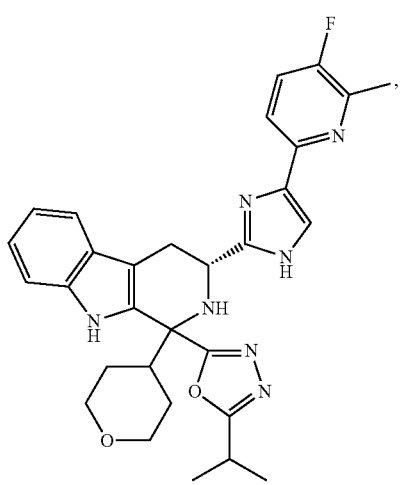
72
-continued
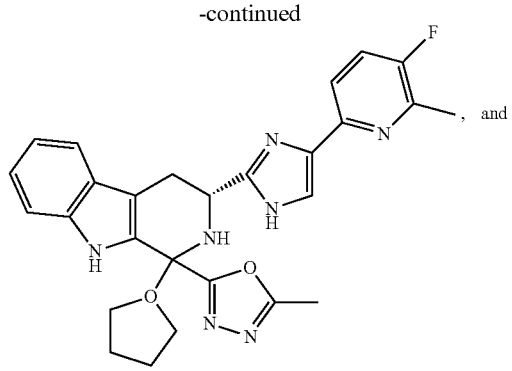
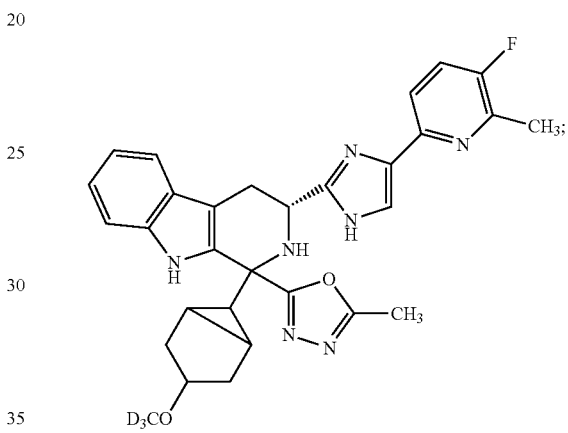
or a pharmaceutically acceptable salt thereof.
14. The compound of claim 13 selected from the group consisting of:
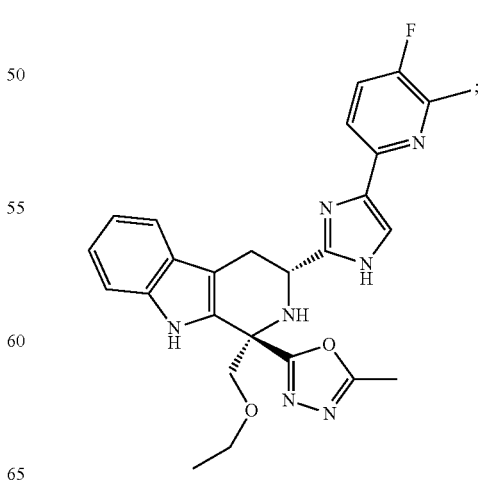
or a pharmaceutically acceptable salt thereof.

15. The compound of claim 13 selected from the group consisting of:

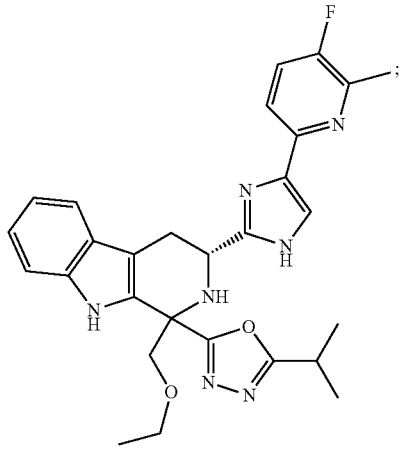 [SMILES: CCOCC1(c2nnc(C(C)C)o2)N[C@@H](c2nc(-c3ccc(F)c(C)n3)c[nH]2)Cc2c1[nH]c1ccccc21]

or a pharmaceutically acceptable salt thereof.

16. The compound of claim 13 selected from the group consisting of:

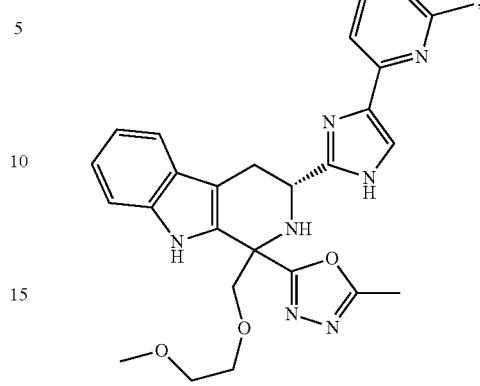

or a pharmaceutically acceptable salt thereof.

17. A pharmaceutical composition comprising a compound of claim 1, or a pharmaceutically acceptable salt thereof, in combination with a pharmaceutically acceptable carrier.

* * * * *